US011484593B2

(12) United States Patent
Ferreira Goncalves et al.

(10) Patent No.: US 11,484,593 B2
(45) Date of Patent: Nov. 1, 2022

(54) ATROPISOMERS OF HALOGENATED TETRAPHENYLBACTERIOCHLORINS AND CHLORINS AND THEIR USE IN PHOTODYNAMIC THERAPY

(71) Applicants: LUZITIN, S.A., Coimbra (PT); UNIVERSIDADE DE COIMBRA, Coimbra (PT)

(72) Inventors: Nuno Paulo Ferreira Goncalves, Coimbra (PT); Tania Patricia Cerca Martins Dos Santos, Coimbra (PT); Goncalo Pereira Nascimento Costa, Coimbra (PT); Carlos Jorge Pereira Monteiro, Coimbra (PT); Fabio Antonio Schaberle, Coimbra (PT); Sonia Correia Alfar, Coimbra (PT); Artur Carlos Reis De Abreu, Coimbra (PT); Maria Miguens Pereira, Coimbra (PT); Luis Guilherme Da Silva Arnaut Moreira, Coimbra (PT)

(73) Assignees: LUZITIN, S.A., Coimbra (PT); UNIVERSIDADE DE COIMBRA, Coimbra (PT)

(*) Notice: Subject to any disclaimer, the term of this patent is extended or adjusted under 35 U.S.C. 154(b) by 404 days.

(21) Appl. No.: 15/559,942

(22) PCT Filed: Mar. 18, 2016

(86) PCT No.: PCT/IB2016/051552
§ 371 (c)(1),
(2) Date: Sep. 20, 2017

(87) PCT Pub. No.: WO2016/151458
PCT Pub. Date: Sep. 29, 2016

(65) Prior Publication Data
US 2019/0167794 A1 Jun. 6, 2019

(30) Foreign Application Priority Data
Mar. 20, 2015 (PT) .......................... 108310

(51) Int. Cl.
*A61K 31/409* (2006.01)
*C07D 487/22* (2006.01)
*A61K 41/00* (2020.01)

(52) U.S. Cl.
CPC ........ *A61K 41/0071* (2013.01); *A61K 31/409* (2013.01); *C07D 487/22* (2013.01)

(58) Field of Classification Search
CPC ... A61K 41/0071; A61K 31/409; A61P 17/06; A61P 27/02; A61P 31/00; A61P 31/04; A61P 31/10; A61P 31/12; A61P 33/02; A61P 33/10; A61P 35/00; C07D 487/22; Y02A 50/30
See application file for complete search history.

(56) References Cited

FOREIGN PATENT DOCUMENTS

WO 2006053707 A1 5/2006
WO 2010047611 A1 4/2010

OTHER PUBLICATIONS

J.M. Dabrowski, et al; New halogenated water-soluble chlorin and bacteriochlorin as photostable PDT sensitizers . . . ; Chemmedchem; vol. 5; 2010; pp. 1770-1780.
M.J. Crossley, et al; Steric effects on atropisomerism in tetraarylprorphyrins; Journal American Chem. Soc.; vol. 109; 1987; pp. 341-348.
J.P. Monteiro Carlos, et al; Separation and atropisomer isolation of ortho-halogenated tetraarylporphyrins by HPLC . . . ; Journal of Porphyrins and Phthalocyanines; vol. 16; No. 3; 2012; pp. 316-323.
A.S. Ressurreicao, et al; Atropisomers of 5,10,15,20-tetrakis . . . ; Journal of Porphyrins and Phthalocyanines; vol. 11; No. 1; 2007; pp. 50-57.

(Continued)

Primary Examiner — Savitha M Rao
Assistant Examiner — Andrew P Lee
(74) Attorney, Agent, or Firm — Lucas & Mercanti, LLP

(57) ABSTRACT

This invention relates to atroipsomers of reduced tetraphenylporphyrin derivatives with halogen atoms (F, Cl, Br) in the ortho positions of the phenyl groups, particularly halogenated tetraphenylchlorins and halogenated tetraphenylbacteriochlorins, which can be used in photodynamic (Continued)

therapy. According to the formulae of the invention, the ortho-phenyl substituents $X^1, X^2, X^3, X^4, X^5, X^6, X^7$ and $X^8$ may be identical or different and represent halogen atoms or hydrogen atoms, provided that at least all of $X^2, X^4, X^6$ and $X^8$ are halogens, and the meta-phenyl substituents $R_1, R_2, R_3$ and $R_4$ are independently chosen from —OH, —OR or —SO$_2$R", where R" are each independently chosen from —Cl, —OH, -aminoacid, —OR, —NHR, or —NR$_2$, where R are alkyl of 1 to 12 carbon atoms or $R_2$ represents cycloalkyl with 2 to 12 carbon atoms. The atropisomers of this invention have the majority of the substituents $R_1, R_2, R_3$ and $R_4$ on the same side of the plane defined by the macrocycle. The invention also relates to an anticancer and/or antimicrobial and/or antiviral pharmaceutical composition where atropisomers $\alpha_4$ and $\alpha_3\beta$ are the main active ingredients, such that the mixture of atropisomers $\alpha_4$ and $\alpha_3\beta$ constitutes more than 70% of the atropisomers present in the active ingredient and/or the atropisomer $\alpha_4$ constitutes more than 20% of the atropisomers present in the pharmaceutical composition.

8 Claims, 18 Drawing Sheets

(56) References Cited

OTHER PUBLICATIONS

International Search Report dated May 24, 2016 for PCT/IB2016/051552.
Written Opinion dated May 24, 2016 for PCT/IB2016/051552.

ATROPISOMERS OF HALOGENATED TETRAPHENYLBACTERIOCHLORINS AND CHLORINS AND THEIR USE IN PHOTODYNAMIC THERAPY

CROSS REFERENCE TO RELATED APPLICATION

This Application is a 371 of PCT/IB2016/051552 filed on Mar. 18, 2016, which claims priority of Portuguese Application No. 108310 filed Mar. 20, 2015, both of which are incorporated herein by reference.

TECHNICAL FIELD

The present application relates to a pharmaceutical composition enriched with atropisomers of halogenated tetraphenylbacteriochlorins and chlorins, its preparation process and use in photodynamic therapy.

BACKGROUND OF THE INVENTION

Sulfonamide tetraphenylchlorins and tetraphenylbacteriochlorins with halogen atoms in the ortho positions of the phenyl groups were found to have particularly useful properties for photodynamic therapy (PDT) (1-4). PDT is a medical treatment that combines the use of a photosensitizing drug, light of a wavelength absorbed by that drug, and molecular oxygen to generate reactive oxygen species (ROS) in the target tissue. The therapeutic effect is mediated by the oxidative stress locally produced by the ROS. Tetraphenylporphyrins, tetraphenylchlorins and tetraphenylbacteriochlorins derivatives are often used as PDT photosensitizers (5). These molecules have phenyl-macrocycle single bonds with hindered rotations. When the phenyl groups contain halogen atoms in the ortho positions, rotation about the single bond between the phenyl group and the macrocycle can be prevented or greatly reduced. Although the steric hindrance of the phenyl-macrocycle single bond rotation can, in principle, be overcome at high temperatures, the half-life of this rotation in halogenated tetraphenylporphyrins, tetraphenylchlorins and tetraphenylbacteriochlorins may be sufficiently long at room temperature and at body temperature to allow for the separation and independent use of stereoisomers possibly existing in this class of molecules. Stereoisomers are most frequently observed as a result of chiral atoms. The enantiomers or diastereomers resulting from the presence of chiral atoms are known to be at the origin of drugs with very differentiated interactions with biological targets. Halogenated tetraphenylbacteriochlorins, tetraphenylchlorins and tetraphenylbacteriochlorins do not have chiral atoms in the macrocycle or in the phenyl groups but have separable stereoisomers because the hindered phenyl-macrocycle single bond may generate a different spatial distribution of bulky substituents. This will be the case of such molecules when they contain non-symmetric substituents in the ortho and/or meta positions and the barrier for the rotation of the phenyl-macrocycle single bond is high. The stereoisomers that result from slow axial rotation are called atropisomers (6). Atropisomers of halogenated tetraphenylporphyrins when the substituents in the two meta positions of the phenyl groups are different (7-9). The compounds of the invention present the first evidence that atropisomers of ortho-halogenated tetraphenylchlorins and of ortho-halogenated tetraphenylbacteriochlorins are separable and that the atropisomers possess differential therapeutic effect as photosensitizers for PDT.

It may be surprising that atropisomers differing only by the conformation around a single bond may generate oxidative stresses with dramatically different therapeutic outcomes. Unexpectedly, the inventors of the present invention found that the enrichment of a mixture of atropisomers in the atropisomers with more voluminous groups on the same side of the plane defined by macrocycle can cure mice with subcutaneously implanted tumors in conditions where the mixture enriched in atropisomers with the same number of voluminous groups on both sides of the macrocycle plane do not cure any animals. The higher PDT efficacy of an atropisomer composition enriched in atropisomers with most of the meta substituents of the phenyl group bound to the macrocycle on the same side of the plane defined by said macrocycle, could not be anticipated by the expert in the field. Indeed, earlier phototoxicity studies with tetraphenylporphyrins seemed to indicate precisely the opposite, i.e., it was suggested that the four isolable atropisomers of "picket fence" tetraphenylporphyrins had no differences in photosensitizing ability (10). Moreover, the two regioisomers of benzoporphyrin derivative monoacid ring A, which is known as verteporfin and is used in clinical practice as a photosensitizer in PDT of age-related macular degeneration, are equally potent photosensitizers of tumor cells in vitro and in vivo (11). Furthermore, the two regioisomers of verteporfin each consist of a racemic mixture of two enantiomers and all enantiomers have similar pharmacological activity (12). Based in all available data, the expert in the field is led to believe that atropisomers of any given photosensitizer interact with light and with oxygen in very similar ways, and conclude the PDT efficacies of the atropisomers must be very similar. The present invention discloses for the first time therapeutically beneficial pharmaceutical compositions of atropisomers of halogenated tetraphenylchlorin or halogenated tetraphenylbacteriochlorin derivatives for use in PDT that are enriched in the atropisomer with all meta substituents of the phenyl group bound to the macrocycle on the same side of the plane defined by said macrocycle (atropisomer $\alpha_4$), such that the relative amount of the atropisomer $\alpha_4$ in the pharmaceutical composition is more than 20%. Against all expectations, it is demonstrated that the PDT efficacy in vitro of the preferred atropisomer $\alpha_4$ can be orders of magnitude larger than the PDT efficacy in vitro of the least photoactive atropisomer $\alpha\beta\alpha\beta$ where the voluminous substituents in the meta positions of adjacent phenyl rings are in opposite sides of the plane defined by the macrocycle ring.

FIG. 1 illustrates the various stereoisomers existing in sulfonamide halogenated tetraphenylbacteriochlorins with halogens in the ortho positions of the phenyl rings and sulfonamide groups in one of the meta positions. The three-dimensional orientation of the atoms of the stereoisomers illustrated in FIG. 1 is different and can be interconverted by the rotation of phenyl-macrocycle single bonds. Such interconversion is very slow at room temperature, or at body temperature, because of the presence of halogen atoms (F, Cl, Br) in the ortho positions of the phenyl rings, which allows for the separation and individual use of each one of the atropisomers. The bold lines in the molecular structures of FIG. 1 indicate that the bolded atoms, and the groups attached thereto, are sterically restricted so as to exist above the plane approximately defined by the macrocycle ring, that is known to be somewhat distorted from the planar geometry but that nevertheless define a restricted spatial orientation of the groups R'. The presence of all R' on the same side of the plane defined by the macrocycle is represented as $\alpha_4$, when three R' are on the same side of the plane and the last R' is on the other side the atropisomer is represented by $\alpha_3\beta$, when two of the R' are on each side and adjacent to each other the representation of the atropisomer is $\alpha_2\beta_2$, and finally when two of the R' are on each side but alternate in the positions with respect to the plane of the macrocycle the representation of the atropisomer is $\alpha\beta\alpha\beta$.

It has been shown that atropisomers of halogenated tetraphenylporphyrins can be separated and may have different molar absorption coefficients in the red region of the electromagnetic spectrum (7, 9). A high molar absorption coefficient in the red, where human tissues have higher transparency than in the other regions of the visible spectrum, is a desirable property for PDT because a dye that absorbs more light is more likely to initiate the cascade of photochemical reactions that generate ROS. On the other hand, atropisomers of halogenated tetraphenylporphyrins, tetraphenylchlorins and tetraphenylbacteriochlorins may have different excited state lifetimes (13) that may influence their PDT efficacy. Shorter triplet lifetimes in aerated solutions are associated with stronger interactions with molecular oxygen, possibly mediated by charge transfer interactions (4). Remarkably, the atropisomers in FIG. 1 have different numbers and different orientations of polar groups on each side of the macrocycle and, consequently, have different polarities. The differences in polarity, shape and excluded molecular volume may provide a basis for their separation, and also have impact on their biological activity. Hence, differences in molar absorption coefficient, excited state lifetime, polarity and excluded molecular volume of the atropisomers may lead to differences in their interactions with molecular oxygen and with biological targets, and have a hitherto undisclosed impact in their PDT activity. Further, based at least on the discussion above, a person of ordinary skill in the art would have expected that atropisomers with higher molar absorption coefficients should be more effective in photodynamic therapy. However, surprisingly, the atropisomer of the present invention that has been shown to be the most efficient in photodynamic therapy is not the atropisomer that absorbs more light.

Tetraphenylbacteriochlorins are relatively unstable (14, 15) and it could not be anticipated that the separation of their atropisomers would be feasible with cost-effective procedures. The introduction of halogen atoms in the ortho positions of the phenyl rings both hinders the rotation of the phenyl-macrocycle bond and stabilizes the macrocycle against oxidation. Hence, halogenated tetraphenylbacteriochlorins have uniquely stable atropisomers, with high phenyl-macrocycle rotational barriers and oxidation potentials as high as those of tetraphenylporphyrins. These properties allow for the separation of the atropisomers of halogenated tetraphenylbacteriochlorins at temperatures equal to, or above, room temperature and in the presence of light and oxygen. Hence, the separation of such atropisomers is cost-effective. There are various ROS that can be generated by photosensitizers. The most important ROS generated by bacteriochlorins in the presence of light of an appropriate wavelength and of molecular oxygen are: singlet oxygen (i.e., the lowest electronically excited state of molecular oxygen), superoxide ion, hydrogen peroxide and the hydroxyl radical (16). The hydroxyl radical is the most reactive of these ROS. It can react with a wide range of biological targets and it may also react with the photosensitizer leading to its bleaching. The electronically excited photosensitizer can be regarded as a very special catalyst that generates ROS when it encounters molecular oxygen. However, when the photosensitizer is bleached by the ROS it cannot generate more ROS. Thus, the efficacy of a photosensitizer is given by a delicate balance between the ability of a photosensitizer to interact strongly with molecular oxygen and its ability to survive that interaction without being bleached (4). The different spatial orientations of the meta substituents in the atropisomers $\alpha_4$, $\alpha_3\beta$, $\alpha_2\beta_2$ and $\alpha\beta\alpha\beta$ may offer distinct and unsuspected interactions with molecular oxygen. This invention demonstrates for the first time that the atropisomers $\alpha_4$, $\alpha_3\beta$, $\alpha_2\beta_2$ and $\alpha\beta\alpha\beta$ possess differential interactions with molecular oxygen and/or ROS manifested in different triplet lifetimes and/or photodecomposition quantum yields. These differences can explain the differential PDT activity of the atropisomers.

SUMMARY OF THE INVENTION

The separation of $\alpha_4$ and $\alpha_3\beta$ atropisomers and the pharmaceutical compositions enriched in the $\alpha_4$ and $\alpha_3\beta$ atropisomers disclosed in this invention are the first evidence that atropisomers possess differential PDT activity and that their differences can be exploited to improve the therapeutic outcome of PDT. "Enriched atropisomer compound" is understood as a mixture of atropisomers obtained in the synthesis of halogenated tetraphenylchlorins and halogenated tetraphenylbacteriochlorins that has been purified to partly remove the least photoactive $\alpha\beta\alpha\beta$ and $\alpha_2\beta_2$ atropisomers present in the statistical atropisomer mixture obtained in the synthesis, where the tetraphenylchlorins and tetraphenylbacteriochlorins have halogen atoms in at least one of the ortho positions of the phenyl groups or, when both ortho positions are occupied by the same halogen atom, have different substituents in the two meta positions of the phenyl groups.

The present invention provides a process for the preparation of a pharmaceutical compositions enriched in atropisomers $\alpha_4$ and $\alpha_3\beta$ which provides a new set of photoactive compounds with higher PDT activity. Included are pharmaceutical compositions where the atropisomers of FIG. 1 with more than half of R' groups on the same side of the plane defined by the macrocycle constitute more than 70% of the total amount of atropisomers present in the composition.

The process of preparation of the pharmaceutical composition of the invention take advantage of the ability to separate atropisomers of halogenated tetraphenylchlorins or halogenated tetraphenylbacteriochlorins at room temperature, or even at temperatures higher than room temperature, possibly in the presence of light and oxygen, using their differences in solubility, or in partition coefficients, in appropriate solvents, or different retention times in chromatography. The different spatial orientation of the polar groups present in the phenyl rings of tetraphenylporphyrins, tetraphenylchlorins or tetraphenylbacteriochlorins give rise to different polarities, shapes and excluded volumes, and allow for the chromatographic separations of the atropisomers. Moreover, differences in solubility, or in partition coefficients, of the atropisomers in different solvents allow for changes in atropisomer composition using selective precipitation, preferential recrystallization, solvent extraction or simply washing the atropisomer mixture with an appropriate solvent. It is possible to reduce the fraction of a given atropisomer of lower PDT efficacy present in the mixture, or to increase the fraction of another atropisomer of higher PDT efficacy also present in the mixture, just by selectively dissolving part of the desired, or undesired, atropisomer with a solvent of appropriate polarity. It is also possible to partially convert one atropisomer into another by thermal or photochemical treatment, such that the molecules acquire enough energy to overcome the hindered rotation of phenyl-macrocycle single bonds, and thus change the composition of the atropisomer mixture.

The present invention discloses the most efficient atropisomers of halogenated tetraphenylchlorins and tetraphenylbacteriochlorins for photodynamic therapy of hyperproliferative disorders and of bacterial and viral infections, and a pharmaceutical composition enriched in the referred two most efficient atropisomers of halogenated tetraphenylchlorins, namely $\alpha_3\beta$ and $\alpha_4$ presented in Formulae (I-C) and (I-D), respectively, characterized by having most of the voluminous substituents in the meta position of the phenyl groups on the same side of the macrocycle plane, Formula (I-C)

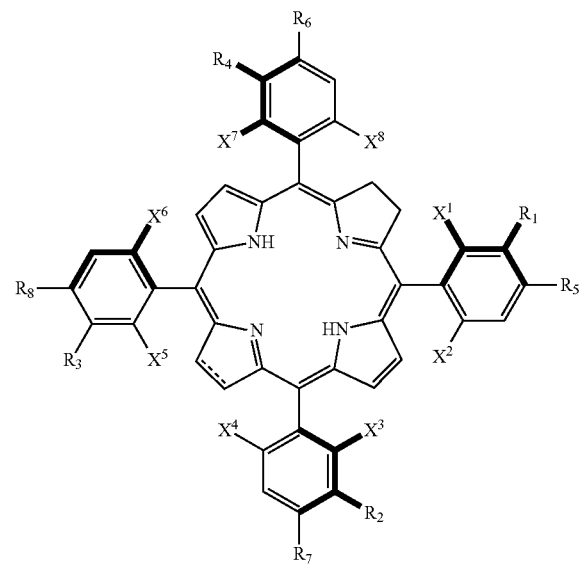

Formula (I-D)

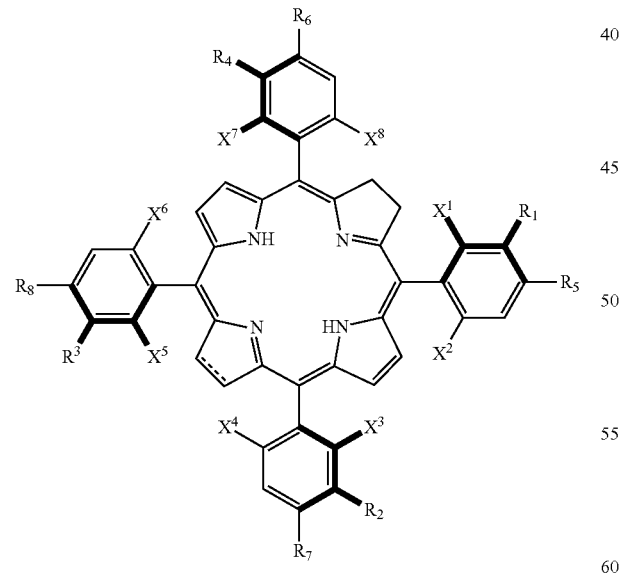

Wherein:
------ represents a carbon-carbon single bond or a carbon-carbon double bond;
the bold lines indicate that the bolded atoms, and the groups attached thereto, are sterically restricted so as to exist above the plane defined by the macrocycle ring;

$X^2$, $X^4$, $X^6$ and $X^8$ are halogen (F, Cl, Br);
$X^1$, $X^3$, $X^5$ and $X^7$ are halogens (F, Cl, Br) or hydrogen;
$R_1$, $R_2$, $R_3$ and $R_4$ are independently —OH, —OR or —SO$_2$R", where R" are each independently chosen from —Cl, —OH, -aminoacid, —OR, —NHR, or —NR$_2$, where R are alkyl of 1 to 12 carbon atoms or $R_2$ represents cycloalkyl with 2 to 12 carbon atoms;
$R_5$, $R_6$, $R_7$ and $R_8$, are independently H, —OH, —OR, —Cl, or —NHR where R are alkyl of 1 to 12 carbon atoms; or pharmaceutically acceptable salts thereof, wherein the relative amount of said atropisomers or their pharmaceutically acceptable salts, is more than 70% of the stereoisomers present in the said pharmaceutical composition.

In another embodiment of the present invention, the pharmaceutical composition is enriched in the more efficient atropisomers of halogenated tetraphenylchlorins and tetraphenylbacteriochlorins, $\alpha_3\beta$ and $\alpha_4$, such that said efficient atropisomers or their pharmaceutically accepted salts constitute (combined) more than 70%, 75%, 80%, 85%, 90% or 95% of the atropisomers present in said pharmaceutical composition.

Hence, the compounds of Formulae (I-C) and (I-D) may be chlorin derivatives having the formulae:

Formula (II-C)

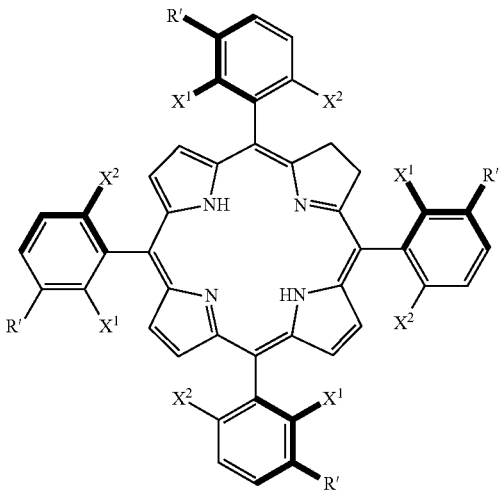

Formula (II-D)

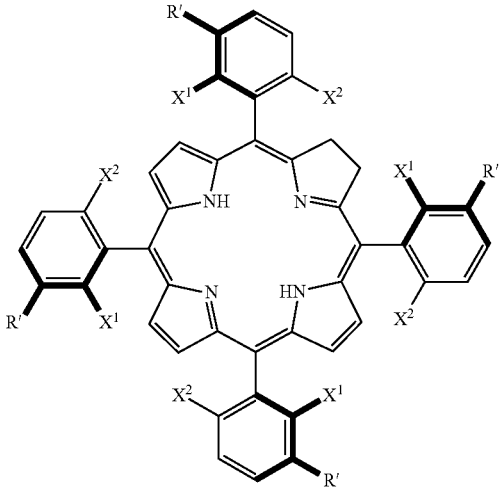

Alternatively, the compounds of Formulae (I-C) and (I-D) may be bacteriochlorin derivatives having the formulae:

Formula (III-C)

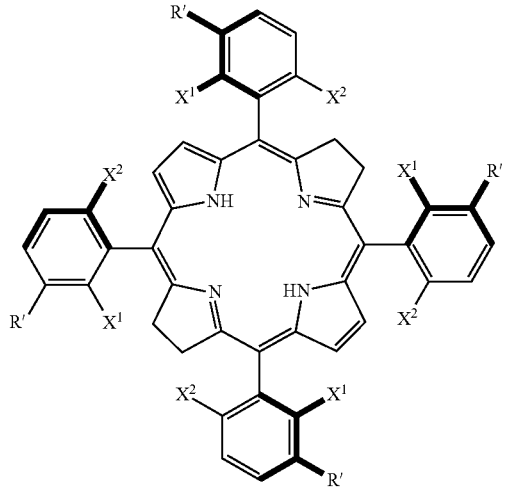

Formula (III-D)

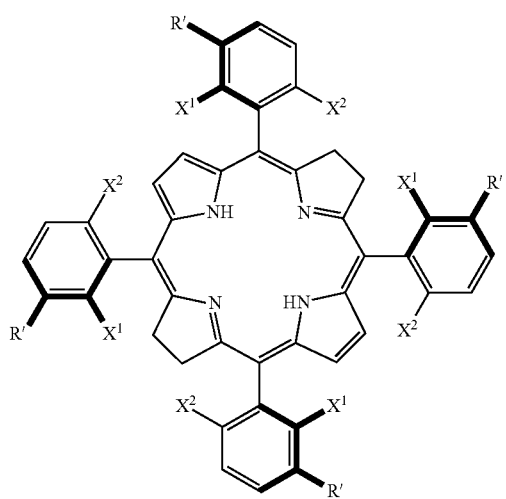

Wherein:
the bold lines indicate that the bolded atoms, and the groups attached thereto, are sterically restricted so as to exist above the plane defined by the macrocycle ring;
Suitably $X^2$ are halogens (F, Cl, Br);
Suitable $X^1$ are hydrogens or halogens (F, Cl, Br);
Suitably R' are —$SO_2R''$, where R'' are each independently chosen from —Cl, —OH, -aminoacid, —OR, —NHR or —$NR_2$, where R are alkyl of 1 to 12 carbon atoms or $R_2$ represents cycloalkyl with 2 to 12 carbon atoms;
or pharmaceutically acceptable salts thereof.

Preferred atropisomers of Formulae (III-C) and (III-D) are those wherein $X^2$ are fluorine or chlorine, and $X^1$ are fluorine or chlorine or hydrogen, and R' are —$SO_2NHR''$ where R'' are alkyl of 1 to 6 carbon atoms.

More specifically, preferred atropisomer $\alpha_4$ of Formula (III-D), wherein $X^2$ are fluorine or chlorine, and $X^1$ are fluorine or chlorine or hydrogen, and R' are —$SO_2NHR''$ where R'' are alkyl of 1 to 6 carbon atoms.

Specific preferred compounds of the invention include the $\alpha_4$ atropisomer of 5,10,15,20-tetrakis(2,6-difluoro-3-N-methylsulfamoylphenyl)bacteriochlorin, of formula LUZ11-D, and the $\alpha_3\beta$ atropisomer of 5,10,15,20-tetrakis(2,6-difluoro-3-N-methylsulfamoylphenyl)bacteriochlorin, of formula LUZ11-C.

Formula (LUZ11-C)

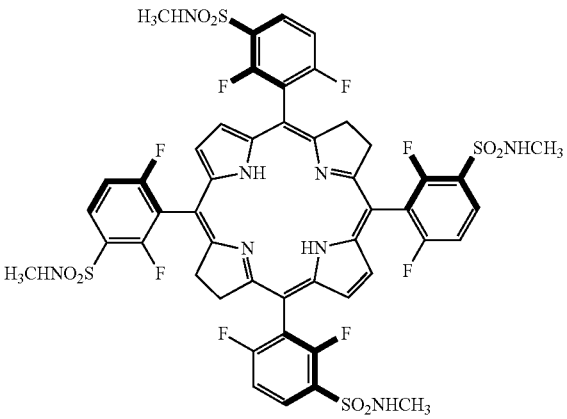

Formula (LUZ11-D)

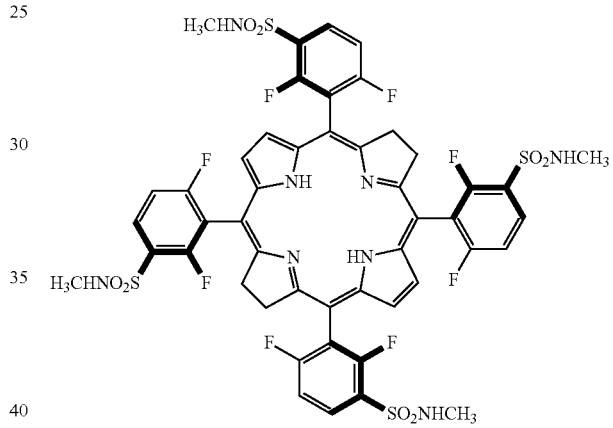

In another embodiment of the present invention, the pharmaceutical composition is enriched in the most efficient atropisomer of halogenated tetraphenylchlorins and tetraphenylbacteriochlorins, $\alpha_4$, which has all the voluminous substituents on the same side of the plane defined by the macrocycle, such that said efficient atropisomer or its pharmaceutically accepted salt constitutes more than 20% of the atropisomers present in the said pharmaceutical composition.

In another embodiment of the present invention, the pharmaceutical composition is enriched in the second most efficient atropisomer of halogenated tetraphenylchlorins and tetraphenylbacteriochlorins, $\alpha_3\beta$, which has most of the voluminous substituents on the same side of the plane defined by the macrocycle, such that said efficient atropisomer or its pharmaceutically accepted salt constitutes more than 60% of the atropisomers present in the said pharmaceutical composition.

In another embodiment of the present invention, the pharmaceutical composition is enriched in the second most efficient atropisomer of halogenated tetraphenylchlorins and tetraphenylbacteriochlorins, $\alpha_3\beta$, which has most of the voluminous substituents on the same side of the plane defined by the macrocycle, such that said efficient atropisomer or its pharmaceutically accepted salt constitutes more than 70%, 75%, 80%, 85%, 90% or 95% of the atropisomers present in the said pharmaceutical composition.

In another embodiment of the present invention, the pharmaceutical composition is enriched in the most efficient atropisomer of halogenated tetraphenylchlorins and tetraphenylbacteriochlorins, $\alpha_4$, such that said efficient atropisomer or its pharmaceutically accepted salt constitutes more than 20%, 30%, 40%, 50%, 60%, 70%, 75%, 80%, 85%, 90% or 95% of the atropisomers present in said pharmaceutical composition.

In another embodiment of the present invention, the pharmaceutical composition further comprises a pharmaceutically accepted carrier.

The present invention also discloses a process for preparation of a pharmaceutical composition enriched in the two most efficient atropisomers of halogenated tetraphenylchlorins and tetraphenylbacteriochlorins, namely atropisomers $\alpha_3\beta$ and $\alpha_4$, which have most of the voluminous substituents on the same side of the plane defined by the macrocycle, comprising an isolation step of the mixture of chlorin or bacteriochlorin atropisomers of formulae:

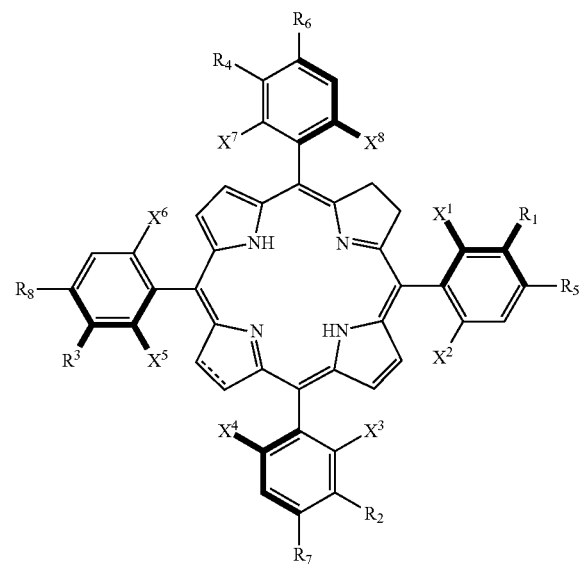

Formula (I-A) = atropisomer $\alpha\beta\alpha\beta$

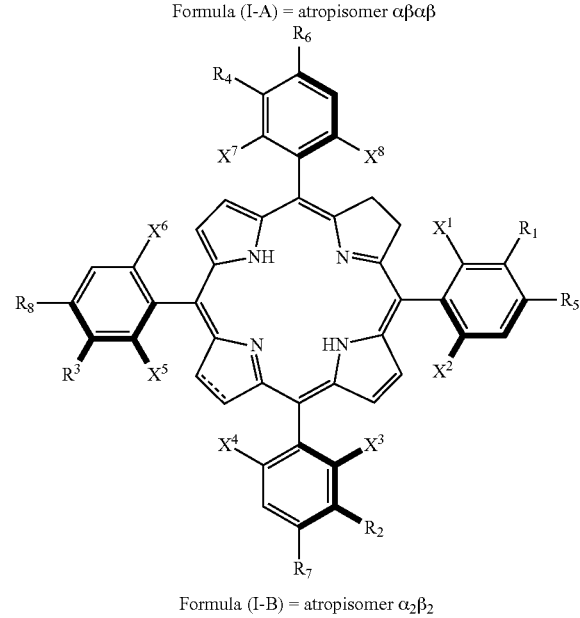

Formula (I-B) = atropisomer $\alpha_2\beta_2$

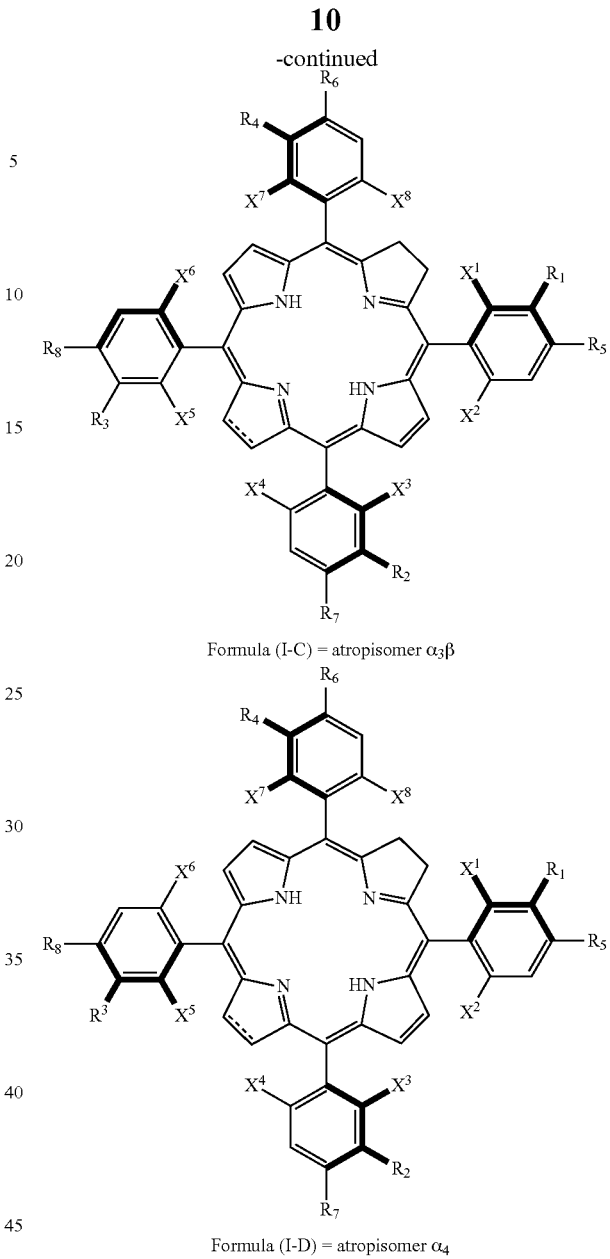

Formula (I-C) = atropisomer $\alpha_3\beta$

Formula (I-D) = atropisomer $\alpha_4$ wherein:
- - - - - represents a carbon-carbon single bond or a carbon-carbon double bond;
the bold lines indicate that the bolded atoms, and the groups attached thereto, are sterically restricted so as to exist above the plane defined by the macrocycle ring;
$X^2$, $X^4$, $X^6$ and $X^8$ are halogen (F, Cl, Br);
$X^1$, $X^3$, $X^5$ and $X^7$ are halogens (F, Cl, Br) or hydrogen;
$R_1$, $R_2$, $R_3$ and $R_4$ are independently —OH, —OR or —SO$_2$R", where R" are each independently chosen from —Cl, —OH, -aminoacid, —OR, —NHR or —NR$_2$ where R are alkyl of 1 to 12 carbon atoms or $R_2$ represents cycloalkyl with 2 to 12 carbon atoms;
$R_5$, $R_6$, $R_7$ and $R_8$ are independently H, —OH, —OR, —Cl, or —NHR where R are alkyl of 1 to 12 carbon atoms;
in which the atropisomers with most of the groups $R_1$, $R_2$, $R_3$ or $R_4$ on the same side of the macrocycle plane are, at least partially, separated by selective precipitation, chromatography, solvent extraction, thermal or photochemical rotational isomerization or selective photodecomposition. Thus, pharmaceutical compositions that are enriched in the desired atropisomers of the formulae herein (e.g., enriched in $\alpha_3\beta$ and $\alpha_4$, $\alpha_3\beta$, or $\alpha_4$) can be obtained by any method, including selective precipitation, chromatography, solvent extraction, thermal or photochemical rotational isomerization or selective photodecomposition, or may be enriched by combining isolated or enriched batches of a single atropisomer or combination of atropisomers to provide a composition having the desired ratio of atropisomers of the formulae herein.

The enrichment of the pharmaceutical composition is possible since it is possible to partially separate the atropisomers $\alpha\beta\alpha\beta$, $\alpha_2\beta_2$, $\alpha_3\beta$ and $\alpha_4$ taking advantage of the difference in polarity and/or excluded volume and/or shape and/or photostability of the atropisomers that have most of the $R_1$, $R_2$, $R_3$ or $R_4$ groups on the same side of the plane with respect to the atropisomers that have the same number of $R_1$, $R_2$, $R_3$ or $R_4$ groups on each side of the plane. This separation is enabled by stability of each atropisomer together with the high barrier for the rotation of the macrocycle-phenyl bond in the atropisomers of Formula (I).

In another embodiment of the present invention, the selective precipitation of the chlorin or bacteriochlorin atropisomers mixture dissolved first in a solvent of higher polarity and then selectively precipitated by the addition to the solution of a solvent with lower polarity, leads to precipitate enriched in atropisomers $\alpha\beta\alpha\beta$ and $\alpha_2\beta_2$ and a solution enriched in the atropisomers $\alpha_3\beta$ and $\alpha_4$ such that their concentrations add to at least 70% (e.g., at least 75%, 80%, 85%, 90%, 95%) of the concentration of all atropisomers present in solution. Mutatis mutantis, the atropisomer mixture may be first dissolved in a solvent of lower polarity and the selective precipitation achieved with the addition of a solvent of higher polarity.

In another embodiment of the present invention, the solvent extraction comprises a first step of dissolving the chlorin or bacteriochlorin atropisomers mixture with a polar solvent; and a second step with the addition of a less polar solvent that forms a liquid-liquid phase separation with the polar solvent thus extracting the least polar atropisomers.

In another embodiment of the present invention, the recrystallization comprises the formation of crystals containing the atropisomers with most of the groups $R_1$, $R_2$, $R_3$ or $R_4$ on the same side of the macrocycle plane that is complementary to the atropisomer composition in the mother liquor.

In another embodiment of the present invention, the thermal or photochemical rotational isomerization comprises a first step of preferentially binding at least one atropisomer of the chlorin or bacteriochlorin atropisomers mixture to a support to which said at least one atropisomer has high affinity; and a second step of providing enough thermal or radiative energy to promote the preferential rotational isomerization of the atropisomers less bound to the support.

In another embodiment of the present invention, the support is preferentially silica gel and the atropisomer preferentially bounded to the support is the atropisomer with the Formula (I-D).

In another embodiment of the present invention, the selective photodecomposition comprises a first step of dissolving the chlorin or bacteriochlorin atropisomers mixture in an aerated solvent; and a second step of irradiating with light that is absorbed by the atropisomer mixture to photodecompose to a greater extent the less photostable atropisomers.

One advantage of the atropisomers $\alpha_3\beta$ and $\alpha_4$ of the present invention lies in their ability to interact strongly with molecular oxygen to generate more reactive oxygen species and produce stronger oxidative stress locally. Another advantage is their increased photostability that increases the turnover of reactive oxygen species for more photons absorbed.

It is also the objective of this invention to disclose the use of the pharmaceutical compositions described herein for the treatment of hyperproliferative disorders including, but are not limited to, cancers or carcinomas, myelomas, psoriasis, macular degeneration, as well as precancerous conditions including, but not limited to Cervical dysplasia and Oral dysplasia.

It is also the objective of this invention to disclose the use of the pharmaceutical compositions described herein for the treatment of infectious diseases caused by microorganisms including, but not limited to viruses, bacteria, rickettsia, mycoplasma, protozoa, fungi; or parasites including, but not limited to generally microscopic or very small multicellular invertebrates, or ova or juvenile forms thereof.

BRIEF DESCRIPTION OF THE DRAWINGS

Without intent to limit the disclosure herein, this application presents attached drawings of illustrated embodiments for an easier understanding.

DESCRIPTION OF THE EMBODIMENTS

Figure 1:
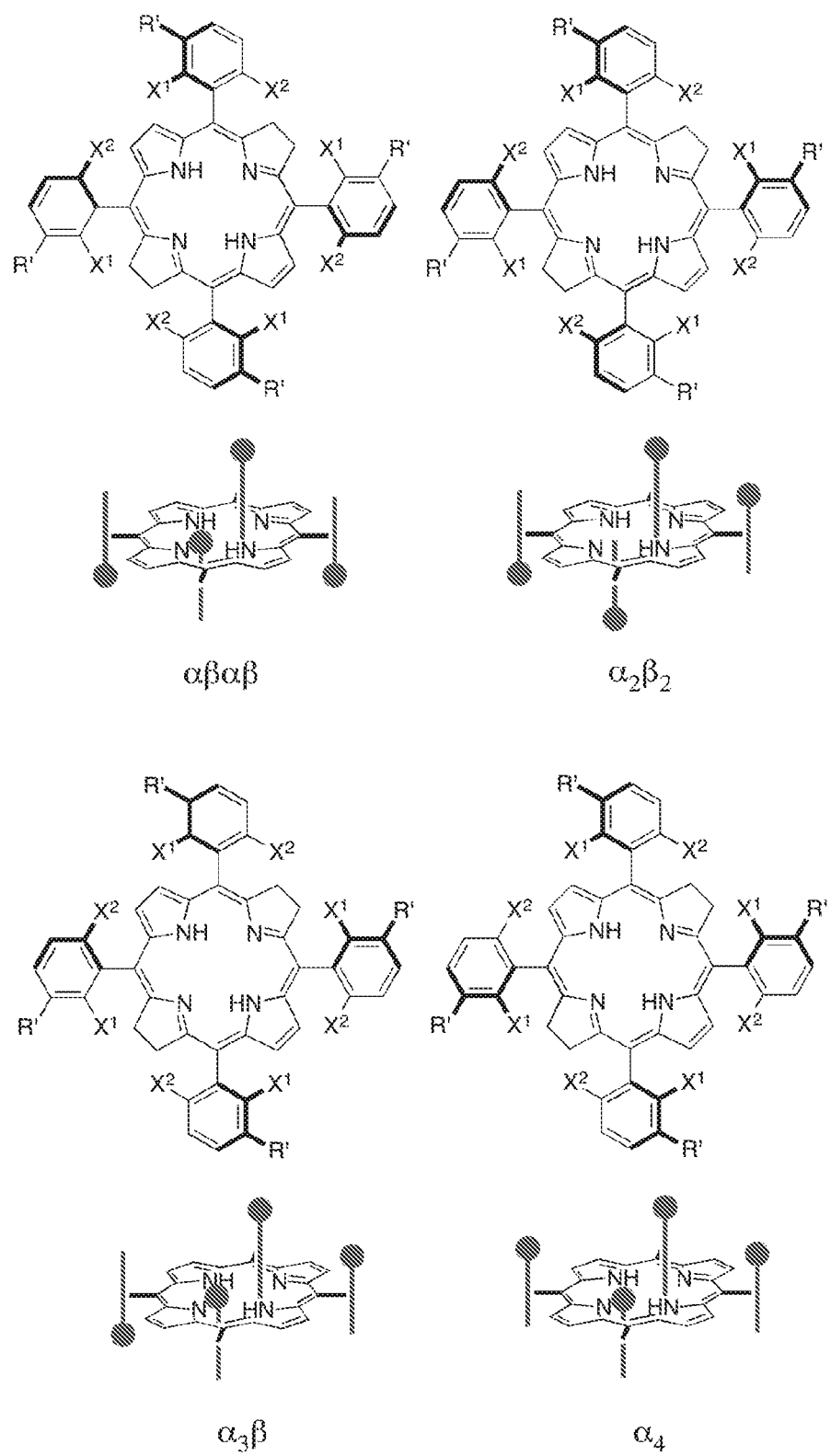
FIG. 1. Atropisomers of halogenated tetraphenylbacteriochlorins, where the bold lines represent bonds that are above the macrocycle plane and define the orientation of the R group above or below that plane, as illustrated by the schemes below the structures. The group R' represents —SO$_2$R", where R" are each independently chosen from —Cl, —OH, -aminoacid, —OR, —NHR and —NR$_2$ where R are alkyl of 1 to 12 carbon atoms or $R_2$ represents cycloalkyl with 2 to 12 carbon atoms. The atoms $X^1$ and $X^2$ are each independently chosen from halogen (F, Cl, Br) and hydrogen atoms, provided that at least all $X^2$ are halogens.

Referring to the drawings, herein are described optional embodiments in more detail, which however are not intended to limit the scope of the present application.

A. Definitions

For the purpose of this application, the following definitions will apply:

The term "stereoisomer" refers to compounds that have identical chemical constitution but differ with regard to the arrangement of atoms or of groups of atoms in the space.

"Atropisomer" is a stereoisomer that results from slow axial rotation around a single bond, may interconvert thermally or photochemically but the interconversion is sufficiently slow at room temperature under ambient light to allow for analytical separation.

"Statistical mixture of atropisomers" of halogenated tetraphenylporphyrins, tetraphenylchlorins or tetraphenylbacteriochlorins refers to the mixture of $\alpha\beta\alpha\beta$, $\alpha_2\beta_2$, $\alpha_3\beta$ and $\alpha_4$ atropisomers obtained in the synthesis where said atropisomers are present in the following ratios: $(\alpha_2\beta_2)/(\alpha\beta\alpha\beta)$ between 1.5 and 2.5, $(\alpha_3\beta)/(\alpha\beta\alpha\beta)$ between 3.0 and 4.5, $(\alpha_4)/(\alpha\beta\alpha\beta)$ between 0.6 and 1.2.

Pharmaceutical compositions "enriched in atropisomers $\alpha_4$ and $\alpha_3\beta$" are understood as mixtures of atropisomers that have a lower relative content of the least photoactive atropisomers $\alpha\beta\alpha\beta$ and $\alpha_2\beta_2$ with respect to the content of the most photoactive atropisomers $\alpha_4$ and $\alpha_3\beta$ present in the statistical mixture of atropisomers obtained in the synthesis of the photoactive compound, such that the atropisomers $\alpha_4$ and $\alpha_3\beta$ constitute more than 70% of said mixture.

"PDT efficacy" is the ability of the photoactive compound to kill cells, bacteria or viruses, or to destroy diseased tissue, for a given drug and light dose. A higher PDT efficacy corresponds to a larger extent of cell death, microorganism death or of tissue necrosis for the same dose of photoactive compound and light.

"Light dose" is a measure of the number of photons delivered to the target where the photoactive compound is present.

"LUZ11" is a code name for 5,10,15,20-tetrakis(2,6-difluoro-3-N-methylsulfamoylphenyl)bacteriochlorin.

"LUZ11-A" is a sample substantially composed by the $\alpha\beta\alpha\beta$ atropisomer of LUZ11. "LUZ11-B" is a sample substantially composed by the $\alpha_2\beta_2$ atropisomer of LUZ11. "LUZ11-C" is a sample substantially composed by the $\alpha_3\beta$ atropisomer of LUZ11. "LUZ11-D" is a sample substantially composed by the $\alpha_4$ atropisomer of LUZ11.

"Substantially composed" in this context refers a composition where the atropisomer is at least 80% of the atropisomers present in the sample.

HPLC is used to mean High Pressure Liquid Chromatography.

As used herein, "hyperproliferative disorders" means those condition disorders sharing as underlying pathology excessive cell proliferation caused by unregulated or abnormal cell growth, and include uncontrolled angiogenesis. Examples of hyperproliferative disorders include, but are not limited to, cancers or carcinomas, myelomas, psoriasis, macular degeneration.

"Hyperproliferative tissue" as used herein means tissue that grows out of control and includes tumors and unbridled vessel growth such as blood vessel growth found in age-related macular degeneration.

As used herein, "infecting agent" denotes invading microorganisms or parasites. As used herein, "microorganism" denotes virus, bacteria, rickettsia, mycoplasma, protozoa, fungi and like microorganisms, and "parasite" denotes infectious, generally microscopic or very small multicellular invertebrates, or ova or juvenile forms thereof.

The invention also provides a pharmaceutical composition, comprising an effective amount a compound described herein (e.g., atropisomers of the formulae herein) and a pharmaceutically acceptable carrier.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention (e.g., atropisomers of the formulae herein) is administered in a pharmaceutically effective amount to a subject in need thereof in a pharmaceutical carrier by intravenous, intramuscular, subcutaneous, intralesional, or intracerebroventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention (e.g., atropisomers of the formulae herein), high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect. Additionally, with photodynamic therapy, the "pharmaceutically effective amount" of the pharmaceutical composition or compound is partially dependent upon other factors such as light dose and oxygen, both of which are required to achieve a therapeutic result. Thus, there will also be an "effective amount" of light as well as amount of oxygen when treating a subject or patient. Other important factors that contribute to the determination of the "pharmaceutically effective amount" of drug, light, and oxygen include drug-to-light intervals (the time between drug administration and illuminating the tissue). Drug-to-light interval is important because, for example, administering a higher drug dose of 50 mg/kg and illuminating the tissue one week later with a light dose of 500 $J/cm^2$ may be as inefficient or ineffective as using a drug dose of 0.01 mg/kg and illuminating the tissue 10 minutes after administration at a light dose of 0.1 $J/cm^2$. The drug elimination (metabolism) by the organism between the administration of the drug and the illumination may decrease the effectiveness of the therapy when the drug-to-light interval increases (becomes longer). However, increasing the drug-to-light interval may lead to a more selective therapy and fewer adverse effectives. Thus, for at least these reasons, drug-to-light interval is an important factor to consider when determining the "pharmaceutically effective amount" of the compositions of the present invention.

In addition to the factors discussed above that affect the determination of the "effective amount" of drug, light, oxygen, and drug-to-light interval, a person of ordinary skill in the art would also take into account the fluence rate of the light (how many photons are delivered per unit area per unit time). Fluence rate is important because the delivery of too many photons too fast may deplete the oxygen in the tissue and render the therapy inefficient or ineffective.

Finally, another parameter that is important for effective treatment is the margin of the tumor or tissue being irradiated. With photodynamic treatments, the irradiated tissue is the primary target of the therapy and will die first, although systemic effects (outside the field of irradiation) may also be observed as a result of the stimulation of the host immune system and/or other cascades of biological effects elicited by the effect of the photodynamic treatment in the primary target. Thus, the selection of the margin is as important in treating a subject or patient using photodynamic therapy, as it would be using surgical treatment.

A decided practical advantage of the present invention is that the compound (e.g., atropisomers of the formulae herein) may be administered in a convenient manner such as by intravenous, intramuscular, subcutaneous, oral, intralesional, or intracerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation or to improve dissolution.

The compound (e.g., atropisomers of the formulae herein) may be administered parenterally or intraperitoneally. Dispersions can also be prepared, for example, in glycerol, liquid polyethylene glycols, and mixtures thereof, and in oils.

The pharmaceutical forms suitable for injectable use include sterile solutions (where soluble) or dispersions and sterile powders for the extemporaneous preparation of sterile injectable solutions or dispersions. In all cases the form must be sterile and must be fluid to the extent that easy syringeability exists. It must be stable under the conditions of manufacture and storage. The carrier can be a solvent or dispersion medium containing, for example, water, DMSO, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion. In many cases it will be preferable to include isotonic agents, for example, sugars or sodium chloride.

Sterile injectable solutions are prepared by incorporating the compound of the invention in the required amount in the appropriate solvent with various of the other ingredients enumerated above, as required, followed by filter sterilization. Generally, dispersions are prepared by incorporating the various sterilized compounds into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yields a powder of the active ingredient plus any additional desired ingredient from previously sterile-filtered solution thereof.

For oral therapeutic administration, the compound may be incorporated with excipients and used in the form of ingestible tablets, buccal tablets, troches, capsules, elixirs, suspensions, syrups, wafers, and the like. Compositions or preparations according to the present invention are prepared so that an oral dosage unit form contains compound concentration sufficient to treat a disorder in a subject.

Some examples of substances which can serve as pharmaceutical carriers are sugars, such as lactose, glucose and sucrose; starches such as corn starch and potato starch; cellulose and its derivatives such as sodium carboxymethylcellulose, ethylcellulose and cellulose acetates; powdered tragacanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, mannitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present.

In another embodiment, the invention provides a composition having a dosage range or a method as described above, wherein the effective amount of the compound delineated herein (e.g., atropisomers of the formulae herein) ranges from about 0.005 μg/kg to about 200 mg/kg. In certain embodiments, the effective amount of the compound of the formulae herein (e.g., atropisomers of the formulae herein) ranges from about 0.02 mg/kg to about 20 mg/kg. In a further embodiment, the effective amount of compound delineated herein ranges from about 0.2 mg/kg to 2 mg/kg. In a further embodiment, the effective amount of the compound delineated herein ranges from about 0.2 mg/kg to 1 mg/kg and the light dose ranges from 30 to 300 J/cm2. In a further embodiment, the effective amount of the compound delineated herein ranges from about 0.5 mg/kg to 2 mg/kg and the light dose ranges from 20 to 150 J/cm2. In a further embodiment, the effective amount of the compound delineated herein ranges from about 0.05 mg/kg (50 ng/mL) to 5 mg/kg, the light dose is between 3 and 300 J/cm2 and the drug-to-light interval is selected from concomitant with the administration of the drug to one week after the administration of the drug.

In other embodiments, the invention provides a method as described above wherein the effective amount of the compound delineated herein (e.g., atropisomers of the formulae herein), in the target tissue at the time of irradiation, ranges from about 0.1 nM to about 50 μM. In certain embodiments, the effective amount ranges from about 10.0 pM to about 10 nM. In another embodiment, the effective amount ranges from about 0.2 nM to about 2 nM. In another embodiment, the effective amount ranges from about 0.1 μM to about 100 μM.

Another object of the present invention is a kit comprising a pharmaceutical composition delineated herein and instructions for administration of the composition. The kit can provide the pharmaceutical composition in any suitable container (i.e., vial, bottle, syringe, ampoule, tube) and include instructions such as for photodynamic therapy/administration (e.g., light exposure instructions, wavelength exposure and duration instructions).

Another object of the present invention is the use of a compound as described herein (e.g., atropisomers of the formulae herein) in the manufacture of a medicament for use in the treatment of a disorder or disease described herein. Another object of the present invention is the use of a compound as described herein (e.g., atropisomers of the formulae herein) for use in the treatment of a disorder or disease described herein.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

B. Precursor Compounds

The porphyrin precursors may be prepared using a process, described in patents PCT/EP/012212 (1) and PCT/PT2009/000057 (2), comprising the following steps:

(i) reduction of the porphyrin with Formula (IV)

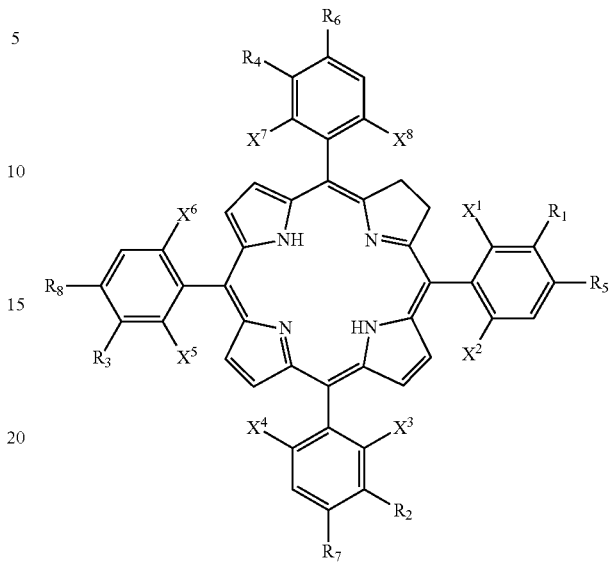

Formula (IV)

Wherein:
a statistical mixture of atropisomers is present;
$X^2$, $X^4$, $X^6$ and $X^8$ are halogen (F, Cl, Br);
$X^1$, $X^3$, $X^5$ and $X^7$ are halogens (F, Cl, Br) or hydrogen;
$R_1$, $R_2$, $R_3$ and $R_4$ are independently —OH, —OR or —SO$_2$R", where R" are each independently chosen from —Cl, —OH, -aminoacid, —OR, —NHR, —NR$_2$ where R are alkyl of 1 to 12 carbon atoms or $R_2$ represents cycloalkyl with 2 to 12 carbon atoms;
$R_5$, $R_6$, $R_7$ and $R_8$, are independently H, —OH, —OR, —Cl, or —NHR where R are alkyl of 1 to 12 carbon atoms,
to the chlorin derivative and/or bacteriochlorin derivatives of formula

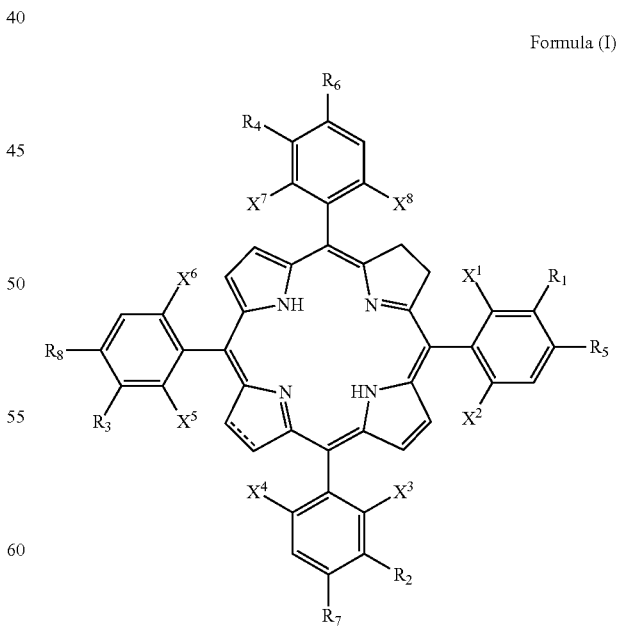

Formula (I)

Wherein:
----- represents a carbon-carbon single bond or a carbon-carbon double bond;

a statistical mixture of atropisomers is present;

using hydrazides and in the presence of organic hindered basis as described in patent PCT/EP/012212 (1); optionally the reducing step can be performed in the absence of solvents and in the absence of bases, as described in patent PCT/PT2009/000057 (2).

Suitably the hydrazide is p-toluenesulphonyl hydrazide, 4-chlorobenzenesulfonic hydrazide, 4,4'-oxybis(benzenesulfonyl) hydrazide, benzenesulfonyl hydrazide, 4-methoxybenzenesulfonyl hydrazide or benzoic hydrazide.

Suitably the sterically hindered base is selected from 1,4-diazabicyclo[2.2.2]octane (DABCO) and 1,8-Diazabicyclo[5.4.0]undec-7-ene (DBU).

Suitably the reduction step is carried out at a temperature from 70 to 200° C. Suitably the reduction step is carried out at a temperature of at least 100° C. Suitably, the reduction step is carried out for at least 5 minutes.

Suitably the reduction step is carried out under an inert atmosphere.

Suitably the option of carrying out the reaction in the absence of solvents requires the use of a temperature that is above the melting point of one of the reactants, such that the other reactant or reactants are partially dissolved, or dispersed, in the melted one. For the solid-state reactions between hydrazides and porphyrin derivatives the solid-state reaction is suitably carried out above the melting point of the hydrazide.

C. Instruments

Elemental analyses were carried out on a Leco TruSpec CHNS elemental analyzer. $^1$H-NMR and spectra were recorded on a Bruker Avance 400 MHz. 1H assignments were made using 2D COSY and NOESY experiments. ESI-FIA TOF High Resolution Mass Spectrometry data were acquired using a Micromass Autospec mass spectrometer. HPLC Shimadzu Prominence equipped with a Diode Array (model SPD 20 AV). Separations were followed at 743 nm, 23° C. on a semi-preparative column Inertsil-Phenyl (250*10 mm; 5 μm).

Absorption spectra were recorded on a Shimadzu UV-2100 spectrophotometer. Fluorescence spectra were measured with a Spex Fluorolog 3 spectrophotometer, with correction for the wavelength dependence system (RCA C31034 photomultiplier). Transient absorption spectra were measured with an Applied Photophysics LKS 60 nanosecond laser flash photolysis kinetic spectrometer, using the third harmonic of a Spectra-Physics Quanta Ray GCR 130-01 Nd/YAG laser for excitation, a Hamamatsu 1P28 photomultiplier and a Hewlett-Packard Infinium oscilloscope (1 GS/s). Flash photolysis measurements were made in the presence of air and in argon saturated solutions. Room-temperature singlet-oxygen phosphorescence was measured at 1270 nm with a Hamamatsu R5509-42 photomultiplier, cooled to 193 K in a liquid nitrogen chamber (Products for Research model PC176TSCE005), following laser excitation of aerated solutions at 355 nm, using an adapted Applied Photophysics spectrometer. The irradiation of bacteriochlorins in the photobleaching experiments employed CW laser emitting at 749+/−3 nm from Omicron Laserage.

D. Methods

A suitable amount of each fraction was dissolved in analytical solvent to a concentration of 0.025 mg/ml. A 15 μl fraction of the prepared solution was then analysed by HPLC with UV-Vis detection. The atropisomers separation was achieved using a Zorbax XDB Eclipse Phenyl column (150*4.6 mm; 5 μm) and a gradient program of two mobile phases: methanol (mobile phase A) and a solution of ammonium acetate buffer, 100 mM, pH 9.5 with methanol at 25:75, v/v (mobile phase B) pumped at a constant flow rate of 1.0 ml/min. The column temperature was kept constant at 20° C. The relative amount of the four LUZ11 atropisomers was determined at 743 nm.

Photobleaching experiments were conducted in methanol: PBS (3:2) solutions, where PBS refers to phosphate-buffered saline solutions. The solutions were irradiated in a cuvette with an optical path of 1 cm using a CW laser emitting at 749±3 nm from Omicron Laserage. The total output power was 640 mW. For each compound, the absorbance was collected in time intervals from few minutes up to hours of irradiation. The initial absorbances of the compounds were ca. 1.0.

The triplet-triplet absorption spectra and the triplet lifetimes of the atropisomers ($\tau_T$) were measured with the transient absorption spectra equipment described above, with excitation at 355 nm, where the solutions had absorbances between 0.25 and 0.30.

Singlet oxygen quantum yields in ethanol were obtained using a procedure described in the literature (17), using phenalenone as reference. The literature value for the singlet oxygen quantum yield obtained with phenalenone in ethanol is $\Phi_\Delta=0.95$ (18).

The pharmaceutical compositions described herein have been evaluated in in vitro studies using tumor cells in culture and diode laser irradiation at 749 nm. HT-29 (human colon carcinoma) and CT26 (mouse colon carcinoma) cells were cultured in Dulbecco's Modified Eagle Medium (Sigma-Aldrich, Steinhelm, Germany) supplemented with 10% heat-inactivated Fetal Bovine Serum (FBS) (Biochrom, Berlin, Germany) and 100 IU/ml penicillin—100 μg/ml streptomycin (Lonza, Verviers, Belgium). Cell lines were maintained in 75 cm$^2$ flasks (Orange Scientific, Brainc-l'Alleud, Belgium) at 37° C. in humidified atmosphere with 5% $CO_2$. Cells at 85-90% confluence were detached with Trypsin-Versene-EDTA solution (Lonza, Verviers, Belgium), counted and seeded in DB Falcon black 96-well plates with clear flat bottom (Franklin Lakes, N.J., USA) at the desired densities, in 100 μl of culture medium, and were allowed to adhere overnight. Test compounds stock solutions were prepared in dimethylsulfoxide and were diluted in culture medium in order to obtain the desired concentration for the incubation with the cells at 37° C. for 24 h in the dark. Each concentration was tested at least in triplicate. After incubation cells were washed once with 200 μl of PBS to remove the non-internalized compound and 100 μl of fresh culture medium was added. Cells were irradiated (each well individually) with a costumer-made diode laser model LDM750.300.CWA.L.M with controller 1201-08P and laser head 1201-08D (Omicron, Rodgau, Germany) emitting at 749 nm. The laser beam was coupled to an optic fiber with an adjustable divergent lens at the end of the fiber, which was fixed on a support and directed perpendicularly to the plate with the cells. The fiber lens was adjusted in order for the irradiation area to exactly match the bottom area of the plate wells, ensuring that each well was individually and completely irradiated with a power density of 8.0 mW/cm$^2$ at the plate level. Laser power measurement was performed with a LaserCheck handheld power meter (Coherent, Inc., Santa Clara, Calif., USA). The irradiation time corresponding to a light dose of 1.0 J/cm$^2$ is 125 seconds.

Cell viability was evaluated 24 h after the irradiation using the resazurin reduction assay. Briefly, resazurin sodium salt (Sigma-Aldrich, Steinhelm, Germany) stock solution (0.1 mg/ml in PBS) was diluted 10% in culture medium without FBS or antibiotics, and 200 μl were added to the cells in each well. Plates were incubated for 3-4 h at 37° C. The absorbance values of each well were measured at 540 nm and 630 nm using a microplate reader Multiskan Ex (Thermo-Electron Corporation, Vartaa, Finland). The cell viability results are expressed as average±SD of the replicated conditions from at least two independent experiments.

The cell viability studies inform on the cytotoxicity of the drugs. This was quantified by expressing cell death relatively to untreated cells (% of control cells, kept in the dark). The results were plotted as dose-response curves (% of cell viability as a function of the concentration of the drug), which allow the determination of the concentration that reduces cell viability in 50% (IC50) and the concentration that reduces cell viability in 90% (IC90) under a given light dose.

The mice used in the present study were BALB/c females weighing 20-25 g (Charles River Laboratories, Barcelona, Spain). The mice were kept on a standard laboratory diet with free access to drinking water. The use of these animals for experimental purposes was approved by the National Veterinary Authority (DGVA authorization no. 0420/000/000/2011). For tumor establishment, 350.000 CT26 cells (CRL-2638™, ATCC-LCG Standards, Barcelona, Spain) were taken up in 0.1 ml PBS and inoculated subcutaneously in the right thigh of each mouse. The tumors were treated 8-10 days after the inoculation, when their diameters reached approximately 5 mm. Mice were treated with a vascular-PDT protocol, that started with the intravenous injection of the compound (0.7 mg/kg) followed 15 minutes later by the irradiation of the tumor with the Omicron diode laser at 749 nm with a laser power of 173 mW. The laser beam was coupled to an optic fiber, with a fixed divergent lens, that was positioned perpendicularly to the tumor surface, in order to irradiate an area of 1.33 cm$^2$ and deliver a total light dose of 55 J.

E. Properties of the Compounds

The absorptivities of the compounds were measured at several concentrations in the μM, and in all cases were observed to follow the Beer-Lambert law. Additionally, the wavelength of maximum absorption ($\lambda_{max}$) in the infrared did not vary in the concentration range studied. This is indicative of little aggregation between the molecules, which exist mostly as monomers at these concentrations in the solvents studied. Table 1 presents infrared molar absorption coefficients ($\varepsilon_{max}$) and wavelength maxima in ethanol obtained for 5,10,15,20-tetrakis(2,6-difluoro-3-N-methylsulfamoylphenyl)bacteriochlorin (sample LUZ11) and its purified atropisomers (samples LUZ11-A, LUZ11-B, LUZ11-C, LUZ11-D). This bacteriochlorin has an intense light absorption in the near infrared, where human tissues are more transparent than in the visible, which is a preferred photosensitizer feature for PDT. The atropisomers have small differences in their $\varepsilon_{max}$. For example, $\varepsilon_{max}$ decreases by 3% from samples LUZ11-A to LUZ11-D. The same table also presents triplet lifetimes ($\tau_T$) in aerated ethanol solutions, photodecomposition quantum yield ($\Phi_{PD}$) in aerated methanol:PBS (3:2) solutions and singlet oxygen quantum yields ($\Phi_\Delta$) in aerated ethanol solutions.

TABLE 1

Photophysical and photochemical properties of LUZ11 samples enriched in its various atropisomers in ethanol, except for the photodecomposition quantum yield ($\Phi_{PD}$) which was measured in methanol:PBS (3:2), and phototoxicity towards CT26 cells in vitro for a light dose of 1 J/cm$^2$.

| Sample | Enriched in atropisomer | $\lambda_{max}$ nm | $\varepsilon/10^3$ (M$^{-1}$ cm$^{-1}$) | $\tau_T$ (air) ns | $\Phi_{PD}/10^{-6}$ | $\Phi_\Delta$ | IC50 (CT26) μM |
|---|---|---|---|---|---|---|---|
| LUZ11-A | αβαβ | 743 | 126 | 257 ± 7 | 15 | 0.39 | 67.35* |
| LUZ11-B | α$_2$β$_2$ | 743 | 137 | 296 ± 33 | 15 | 0.35 | 1.460 |
| LUZ11-C | α$_3$β | 743 | 137 | 268 ± 23 | 12 | 0.50 | 0.816 |
| LUZ11-D | α$_4$ | 743 | 122 | 266 ± 15 | 9 | 0.49 | 0.207 |

*Extrapolated from non-linear regression curve.

The transient lifetimes were measured at 400, 610 and 790 nm. All triplet decays were clearly mono-exponential and in air-saturated ethanol the triplet lifetimes were in the range of 200-300 nanoseconds. Such values are consistent with diffusion limited energy transfer from the triplet state of the photosensitizer to molecular oxygen through a charge-transfer interaction (4). The photodecomposition utilized a CW laser emitting at 749±3 nm and total power of 640 mW. All compounds followed a mono-exponential decrease in their absorptivity intensities. The most photostable atropisomer in Table 1 is sample LUZ11-D, with a photodecomposition quantum yield $\Phi_{PD}=9\times10^6$.

All the singlet oxygen emissions measured in aerated ethanol solutions are very well described by mono-exponential decays, with typical singlet oxygen lifetimes ($\tau_\Delta \approx 16$ μs). The $\Phi_\Delta$ values of Table 1 were obtained by the procedures described above.

Using the methods described above and further detailed in the examples below, the concentrations of the various atropisomers required to kill 50% of CT26 cells in vitro under a laser light dose of 1 J/cm$^2$ are also presented in Table 1. The dramatic difference in phototoxicities between samples LUZ11-A and LUZ11-D could not be anticipated from the known mechanism of action of PDT, which is based on the oxidative stress caused by the generation of ROS when a photosensitizer absorbs light in the presence of oxygen. In fact, it could not be anticipated that atropisomer αβαβ having only small differences in light absorption and in the efficiency in the generation of singlet oxygen with respect to α$_4$ would be a much poorer photosensitizer. In earlier uses of photosensitizers in PDT it has not been appreciated that atropisomers with the same number of voluminous groups on either side of the plane defined by the macrocycle do not contribute appreciably to the PDT efficacy of the atropisomer mixture. It is a central object of the present invention to describe, for the first time, pharmaceutical compositions enriched in atropisomers α$_3$β and α$_4$, where these atropisomers represent more than 70% of all atropisomers present in the mixture, that surpass the PDT efficacy of the statistical atropisomer mixture obtained from its synthesis. It is also an object of the present invention to describe a pharmaceutical composition enriched in atropisomer α$_3$β, where this atropisomer represents more than 60% of all atropisomers present in the mixture and improves its PDT efficacy. It is also an object of the present invention to describe a pharmaceutical composition enriched in atropisomer $\alpha_4$, where this atropisomer represents more than 20% of all atropisomers present in the mixture and improve its PDT efficacy. It is a further object of the present invention to describe, for the first time, the use of chemical separation processes at temperatures higher than 20° C. and in the presence of light and oxygen, to enrich the atropisomer mixture in the atropisomers $\alpha_3\beta$ and $\alpha_4$ of tetraphenylbacteriochlorins previously regarded as labile.

EXAMPLES

This invention will now be described in more detail in the following non-limiting EXAMPLES, with reference to the following drawings:

Example 1

Synthesis and Characterization of the Atropisomers Present in a Fluorinated Sulfonamide Tetraphenylchlorin The chemical synthesis of a mixture of atropisomers complying with Formula (II),

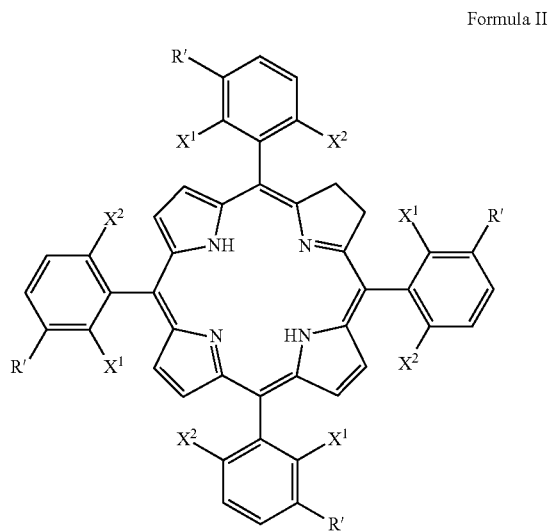

Figure 2:
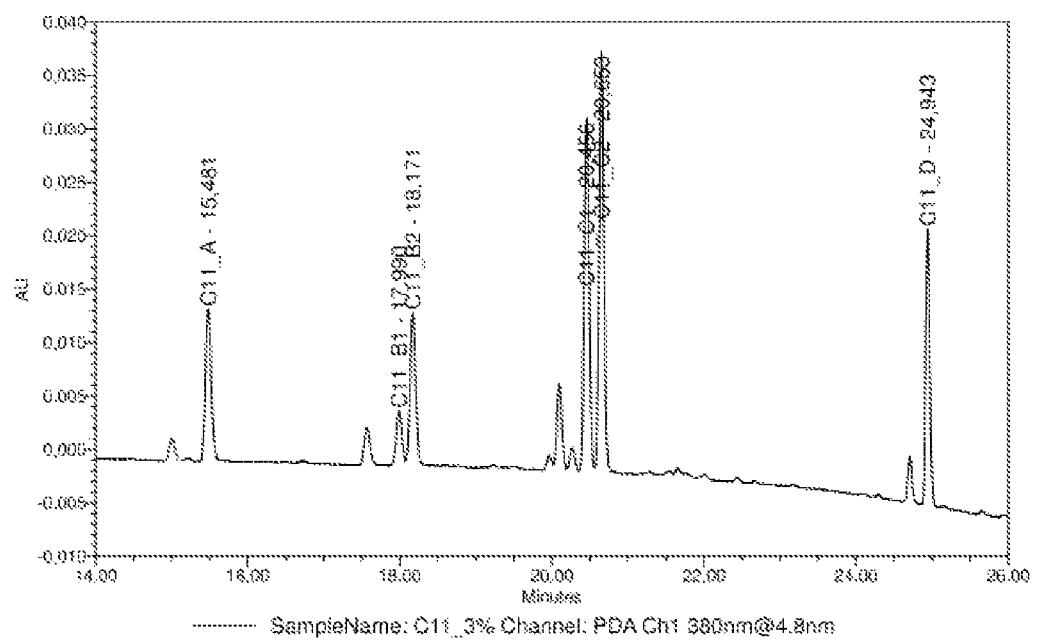
FIG. 2. UHPLC chromatogram with detection at 380 nm of a 5,10,15,20-tetrakis(2,6-difluoro -3-N-methylsulfamoylphenyl)chlorin sample obtained in the synthesis without solvent.

Formula II wherein $X^1$ and $X^2$ are fluorine atoms and R' is the group —$SO_2NHCH_3$ and their characterization, was conducted as follows:

The synthesis of 5,10,15,20-tetrakis(2,6-difluoro-3-N-methylsulfamoylphenyl)chlorin is performed by reaction of p-toluenesulphonyl hydrazide (700±10 mg) with 5,10,15,20-tetrakis(2,6-difluoro-3-N-methylsulfamoylphenyl) porphyrin (100±10 mg) at a pressure below 0.6 mbar, heating to 140±1° C. for 15 minutes. After cooling to room temperature the reaction crude is dissolved in dichloromethane ($\approx$50 mL) and sequentially washed with sodium hydroxide (0.5 M) and water (3 times). The organic phase was dried with anhydrous sodium sulfate, filtrated and then concentrated. The mixture of compounds was precipitated with hexane. The solid was dissolved in dimethoxyethane (DME) (20 mL) and $FeCl_3 \cdot 6H_2O$(1 equiv.) was added to the solution, followed by 0.1 mL of hydrogen peroxide (3% in water). The final solution was kept under stirring, at room temperature. After 90 minutes, 0.1 mL of hydrogen peroxide (3% in water) was added and the reaction was stopped when the absorption peak of bacteriochlorin ($\approx$750 nm) had disappeared (90 minutes). Diethyl carbonate was added to the solution and the organic phase was then washed twice with a saturated solution of sodium thiosulfate, twice with distilled water, and then dried over anhydrous $Na_2SO4$. The solvent was evaporated and purified by column chromatography with silica gel (dichloromethane/ethyl acetate). The 5,10,15,20-tetrakis(2,6-difluoro-3-N-methylsulfamoylphenyl)chlorin containing the mixture of atropisomers was obtained with 80±5% yield (80±5 mg). FIG. 2 presents the UHPLC chromatogram with detection at 380 nm. The separation of all chlorin atropisomers was achieved using an Acquity BEH C18 column (150*2.1 mm; 1.7 μm) and a gradient program of three mobile phases: Ammonium acetate buffer, 50 mM (mobile phase A), Isopropanol (mobile phase B) and a solution of methanol:acetonitrile (70:30 v/v) (mobile phase C) pumped at a constant flow rate of 0.2 ml/min). The column temperature was kept constant at 40° C. Remarkably, the largest peak, expected for the statistically favourable formation of the $\alpha_3\beta$ atropisomer, is split in two. This is assigned to the differentiation between the position of the reduced pyrrole group of the macrocycle between two phenyl groups with voluminous substituents on the same side of the macrocycle plane, and the position of the reduced pyrrole group between two phenyl groups with voluminous substituents in different sides of that plane. This example illustrates that it is possible to separate the atropisomers of tetraphenylchlorin derivatives at 40° C. by virtue of an unexpected combination of the stability of the tetraphenylchlorins and slowness of rotation of the macrocycle-phenyl bonds at this temperature.

Figure 3:
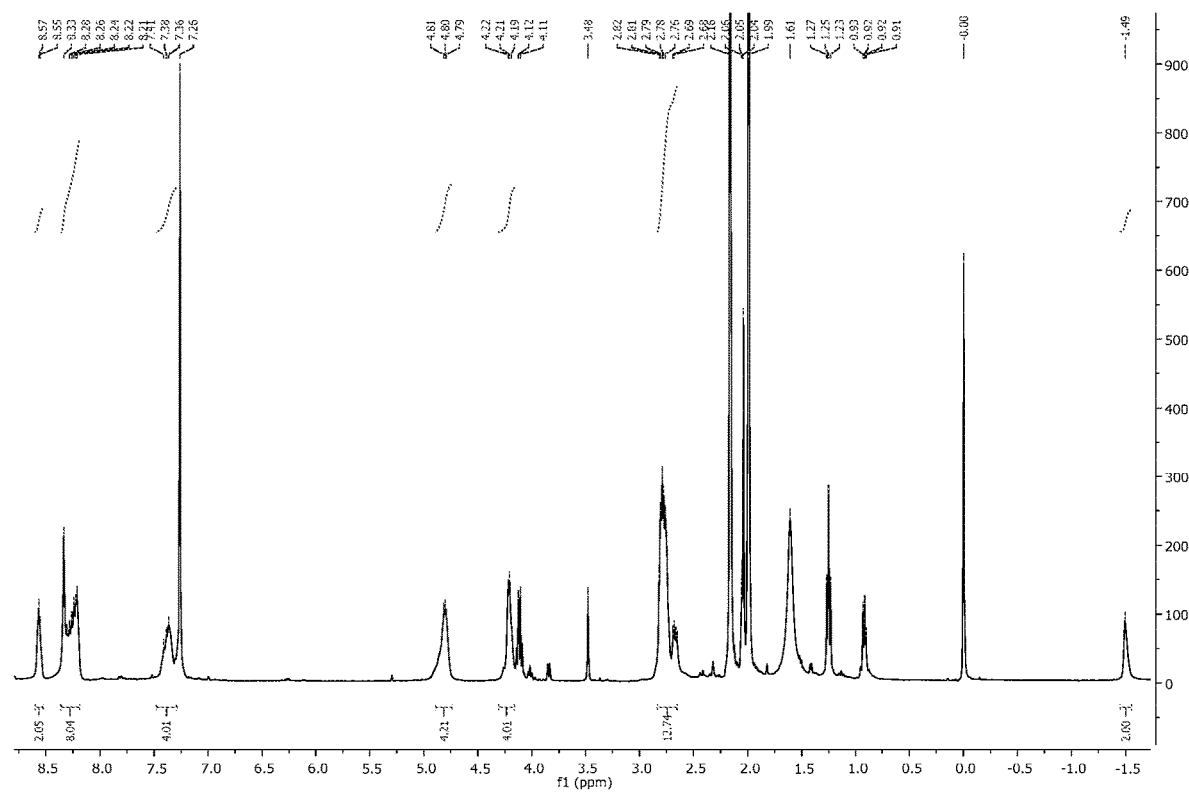
FIG. 3. $^1$H-NMR spectrum of a 5,10,15,20-tetrakis(2,6-difluoro-3-N-methylsulfamoylphenyl)chlorin sample obtained in the synthesis without solvent.

The NMR and MS of the tetraphenylchlorin sample are as follows: NMR $^1H$ (400 MHz, $CDCl_3$), δ, ppm: 8.57 (m, 2H, β-H); 8.33-8.21 (m, 8H, Ar—H+β-H); 7.41-7.36 (m, 4H, Ar—H); 4.81-4.79 (m, 4H, NH); 4.22-4.19 (m,4H, β-H); 2.82-2.76 (m, 12H, $CH_3$); -1.49 (s, 2H, NH). The NMR spectrum is shown in FIG. 3.

MS (ESI-FIA-TOF): m/z calcd for ($C_{48}H_{37}F_8N_8O_8S_4$) $[M+H]^+$: 1133.1484, found $[M+H]^+$: 1133.1466

Example 2

Synthesis, Characterization and Separation of the Atropisomers Present in a Fluorinated Sulfonamide Tetraphenylbacteriochlorin The chemical synthesis of a mixture of atropisomers complying with Formula (III), Formula III

Figure 4:
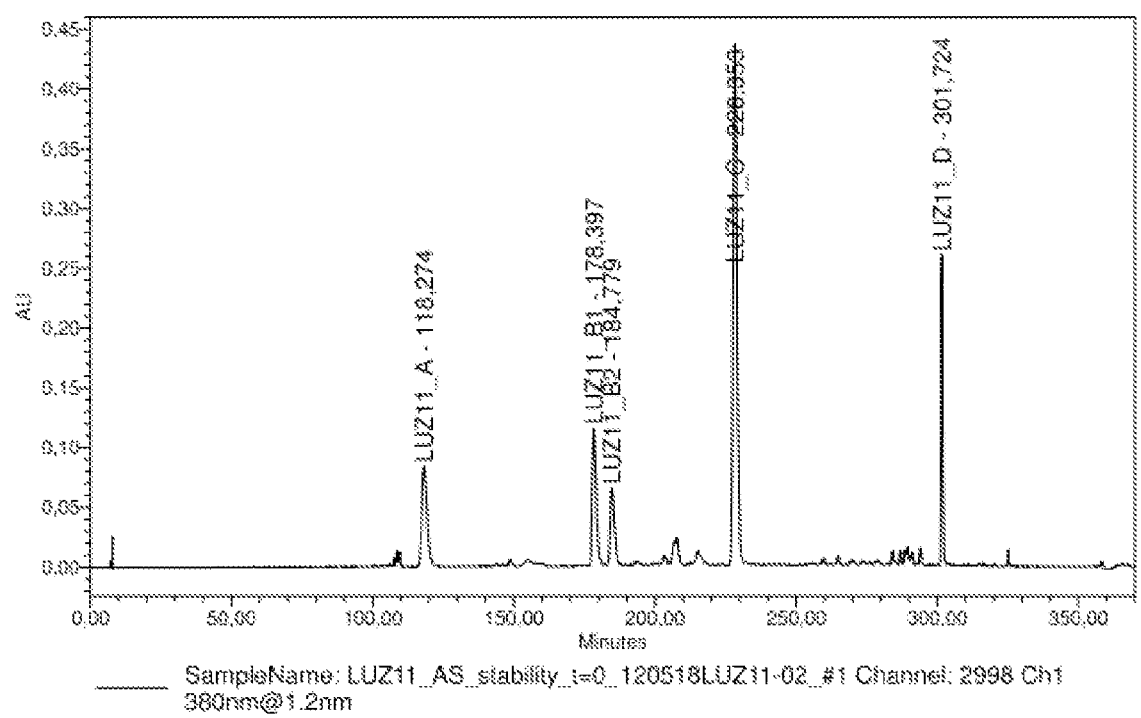
FIG. 4. HPLC chromatogram of a 5,10,15,20-tetrakis(2,6-difluoro-3-N-methylsulfamoylphenyl)bacteriochlorin sample obtained in the synthesis without solvent.

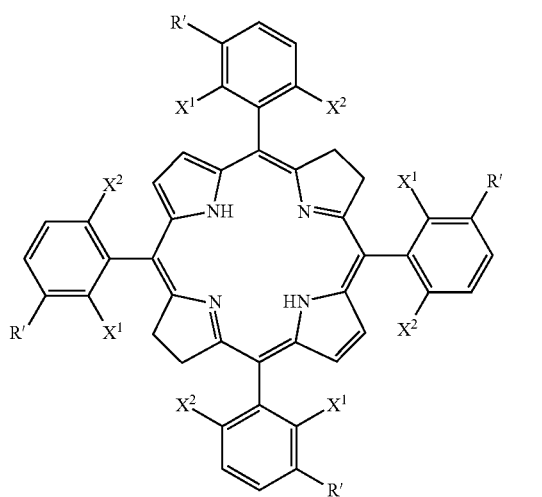

wherein $X^1$ and $X^2$ are fluorine atoms and R' is the group —$SO_2NHCH_3$, their separation in each one of the atropisomers and their characterization, was conducted as follows: The synthesis of 5,10,15,20-tetrakis(2,6-difluoro-3-N-methylsulfamoylphenyl) bacteriochlorin (LUZ11) is performed by the direct reaction of p-toluenesulphonyl hydrazide (7±0.1 g) with 5,10,15,20-tetrakis(2,6-difluoro-3-N-methylsulfamoylphenyl)porphyrin (1±0.05 g), at a pressure below 0.6 mbar, heating to 140° C.±1° C. for 60 minutes. After cooling to room temperature the reaction crude is dissolved and purified by column chromatography with silica gel (dichloromethane/ethyl acetate). The 5,10,15,20-tetrakis(2,6-difluoro-3-N-methylsulfamoylphenyl)bacteriochlorin containing a mixture of four atropisomers was obtained with 85±5% yield (850±50 mg) with HPLC purity>95%. FIG. 4 presents the HPLC chromatogram of the LUZ11 sample. A suitable amount of sample was dissolved in analytical solvent (solution of N,N-dimethylformamide with Tween20 at 2% w/v). A 20 µl fraction of the prepared solution was then analysed by HPLC with UV-Vis detection. The atropisomers separation was achieved using an Inertsil Phenyl column (250*4.6 mm; 5 µm) and a gradient program of three mobile phases: methanol (mobile phase A), a trimethylamine solution, pH 7.0 (mobile phase B) and a mixture of triethylamine solution pH 7.0 with methanol (25:75, v/v) (mobile phase C) pumped at a constant flow rate of 0.5 ml/min). The column temperature was kept constant at 60° C. This example illustrates that it is possible to separate the atropisomers of tetraphenylbacteriochlorins derivatives at 60° C. by virtue of a very unexpected combination of the stability of the tetraphenylbacteriochlorins and slowness of rotation of the macrocycle-phenyl bonds at this temperature.

The NMR and MS of the isolated LUZ11 sample are as follows:

NMR $^1$H: (400 MHz, CDCl$_3$) δ ppm: 8.24 (m, 4H, β-H); 8.01-7.99 (m, 4H, Ar—H); 7.39-7.31 (m, 4H, Ar—H); 4.76-4.67 (m, 4H, NH); 4.05 (s,8H, β-H); 2.81-2.70 (m, 12H, CH$_3$); -1.39 (s, 2H, NH).

Figure 5:
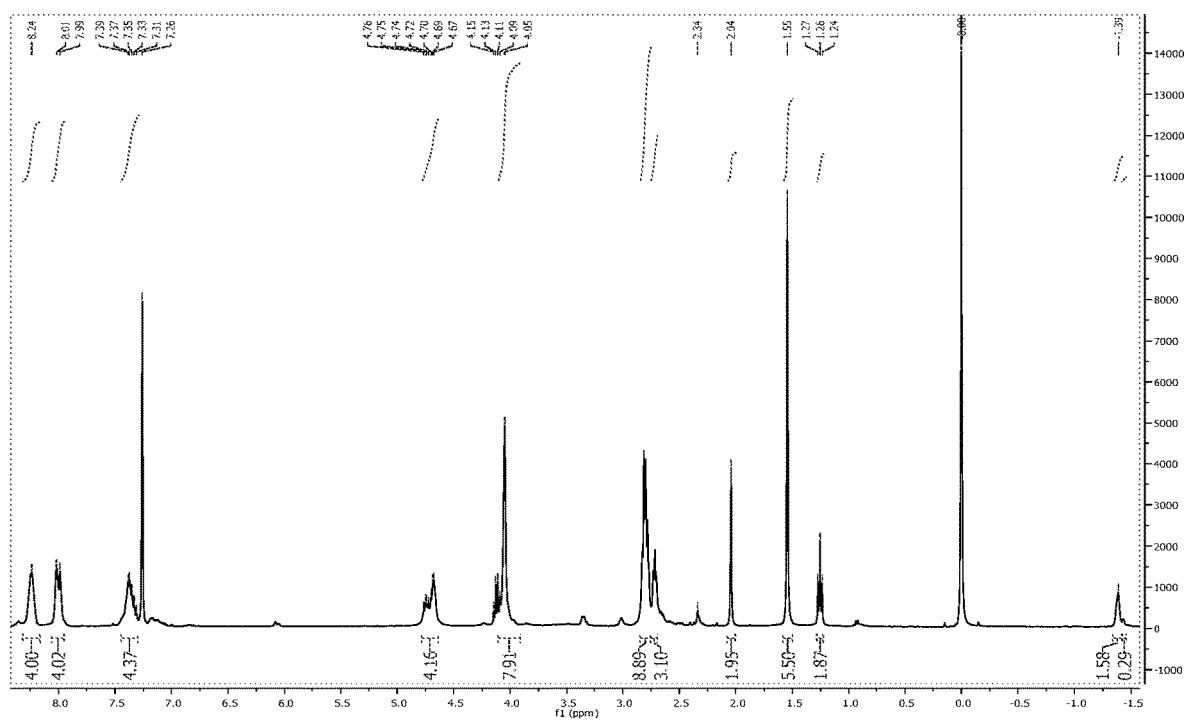
FIG. 5. $^1$H-NMR spectrum of 5,10,15,20-tetrakis(2,6-difluoro-3-N-methylsulfamoylphenyl)bacteriochlorin sample obtained in the synthesis without solvent.

The NMR spectrum is shown in FIG. 5.

MS (ESI-FIA-TOF): m/z calcd for $C_{48}H_{39}F_8N_8O_8S_4$ [M+H]$^+$: 1135.1640, found [M+H]$^+$: 1135.1612.

Elemental Analysis ($C_{48}H_{38}F_8N_8O_8S_4.H_2O$): calcd. C 50.00, H 3.50, N 9.72, S 11.12, found C 49.88, H 3.47, N 9.38, S 10.94.

The isolation of the four atropisomers present in the LUZ11 sample synthesized as above was accomplished dissolving 300 mg of the LUZ11 sample in 12 mL of dimethylformamide (DMF) and 2.5 mL of water. After sonication for 5 minutes to obtain complete solubilization of the LUZ11 sample, the atropisomers were separated by HPLC using a preparative column and the following general conditions: column=Inertsil-Phenyl (250*10 mm, 5 µm), flow=3 ml/min, detection=743 nm, oven=23° C., injection volume=100 µl, run time=70 min, mobile phase A=acetonitrile (ACN) gradient grade, mobile phase B=water. The gradients employed in the separation of each atropisomer are presented in Table 2:

TABLE 2

Gradients used on the separation of LUZ11 atropisomers by preparative HPLC.

| | Sample | | | |
|---|---|---|---|---|
| Time (min) | LUZ11-A (ACN:Water) | LUZ11-B (ACN:Water) | LUZ11-C (ACN:Water) | LUZ11-D (ACN:Water) |
| 0 | 54:46 | 56:44 | 57:43 | 60:40 |
| 35 | 54:46 | 56:44 | 57:43 | 67:33 |
| 45 | 54:46 | 56:44 | 57:43 | 67:33 |
| 50 | 95:5 | 56:44 | 57:43 | 67:33 |
| 52 | 95:5 | — | 57:43 | — |
| 54 | 95:5 | 95:5 | 95:5 | 95:5 |
| 58 | 95:5 | 95:5 | 95:5 | 95:5 |
| 60 | — | 95:5 | 95:5 | 95:5 |
| 64 | 54:46 | 56:44 | 95:5 | 60:40 |
| 65 | 54:46 | 56:44 | 95:5 | 60:40 |
| 68 | 54:46 | 56:44 | 57:43 | 60:40 |
| 70 | 54:46 | 56:44 | 57:43 | 60:40 |

Figure 6:
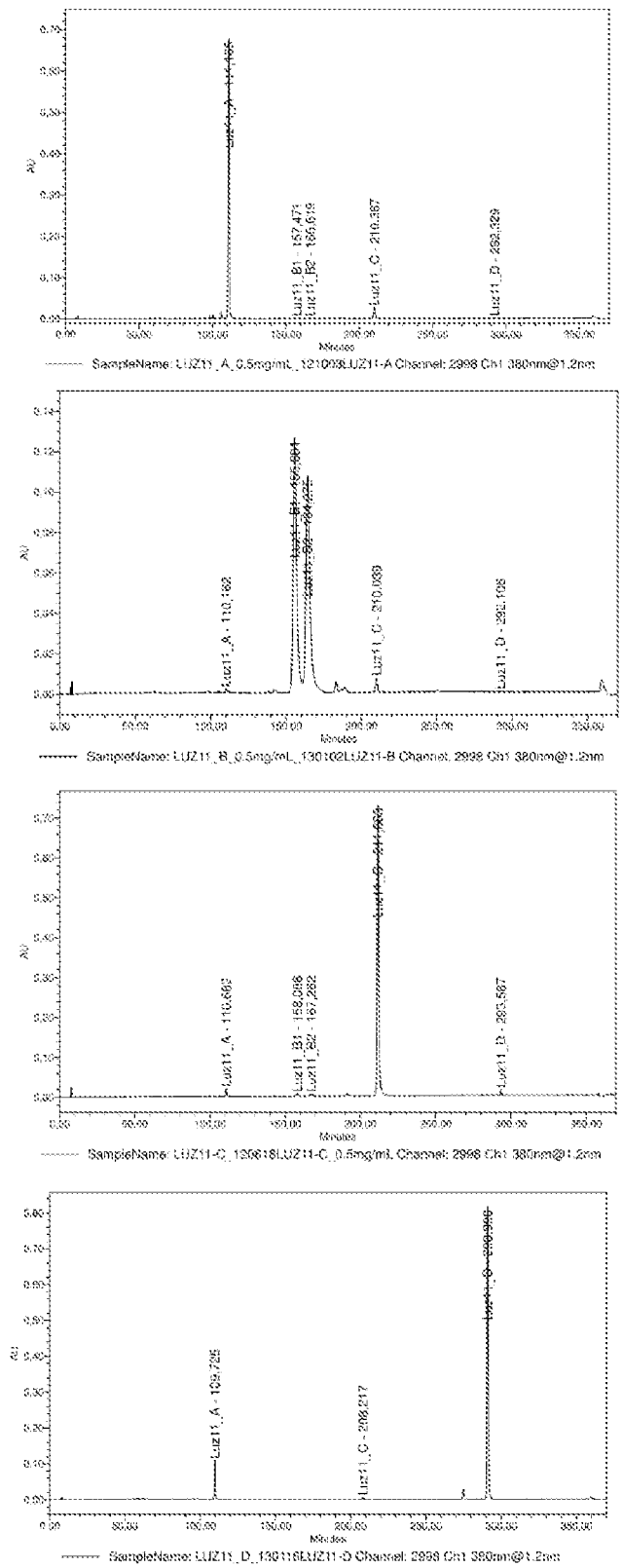
FIG. 6. HPLC chromatograms of LUZ11-A, LUZ11-B, LUZ11-C and LUZ11-D samples separated by preparative HPLC.
Figure 7:
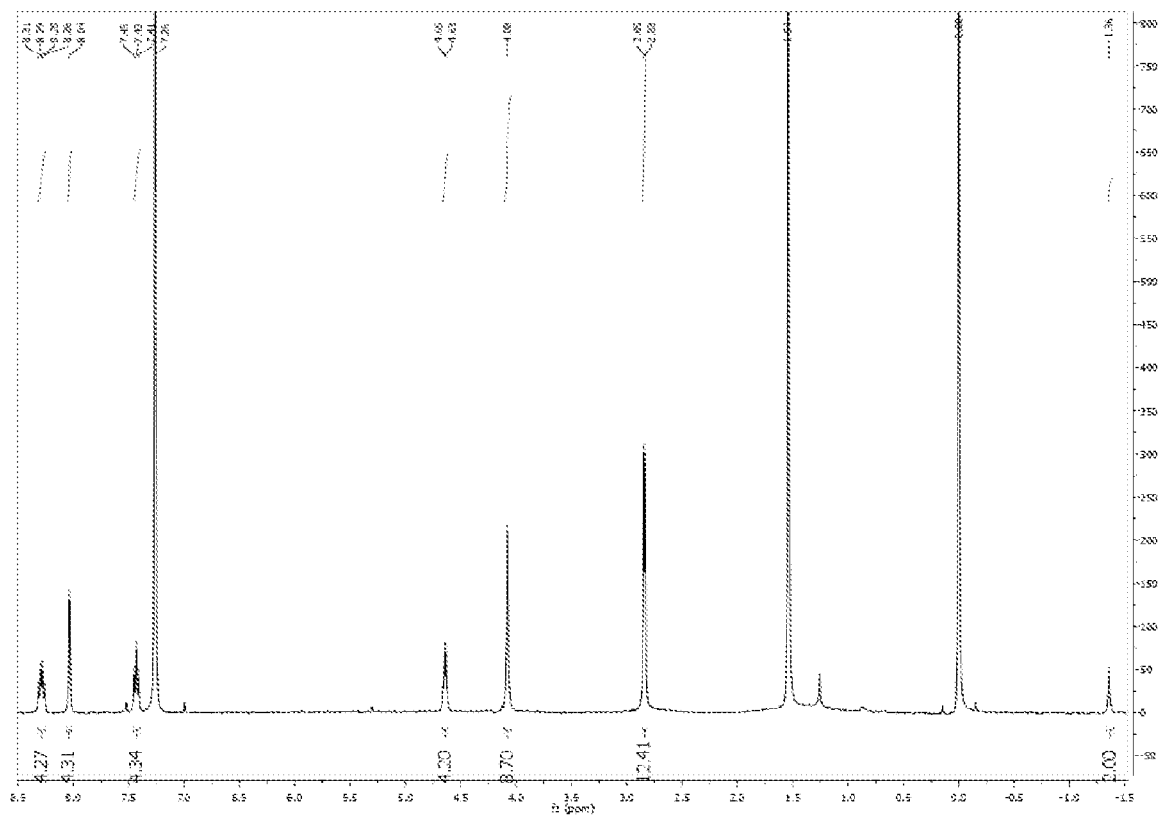
FIG. 7. $^1$H-NMR spectrum of LUZ11-A sample.

FIG. 6 presents the HPLC chromatograms of the separated LUZ11-A, LUZ11-B, LUZ11-C and LUZ11-D samples obtained with the method described above. The four samples were also characterized by NMR spectroscopy, mass spectrometry and elemental analysis. The results are presented below:

LUZ11-A (mostly αβαβ):

NMR $^1$H (400 MHz, CDCl$_3$): δ, ppm: 8.31-8.26 (m, 4H, Ar—H); 8.04 (s, 4H, β-H); 7.45-7.41 (m, 4H, Ar—H);

4.65-4.63 (m, 4H, NH); 4.08 (s, 8H, β-H); 2.85-2.83 (m, 12H, CH$_3$); -1.36 (s, 2H, NH). The NMR spectrum is shown in FIG. 7.

MS (ESI-FIA-TOF): m/z calcd for (C$_{48}$H$_{39}$F$_8$N$_8$O$_8$S$_4$) [M+H]$^+$: 1135.1640, found [M+H]$^+$: 1135.1665.

Elemental Analysis (C$_{48}$H$_{38}$F$_8$N$_8$O$_8$S$_4$): calcd. C 50.79, H 3.37, N 9.87, found C 50.27, H 3.89, N 9.30.

Figure 8:
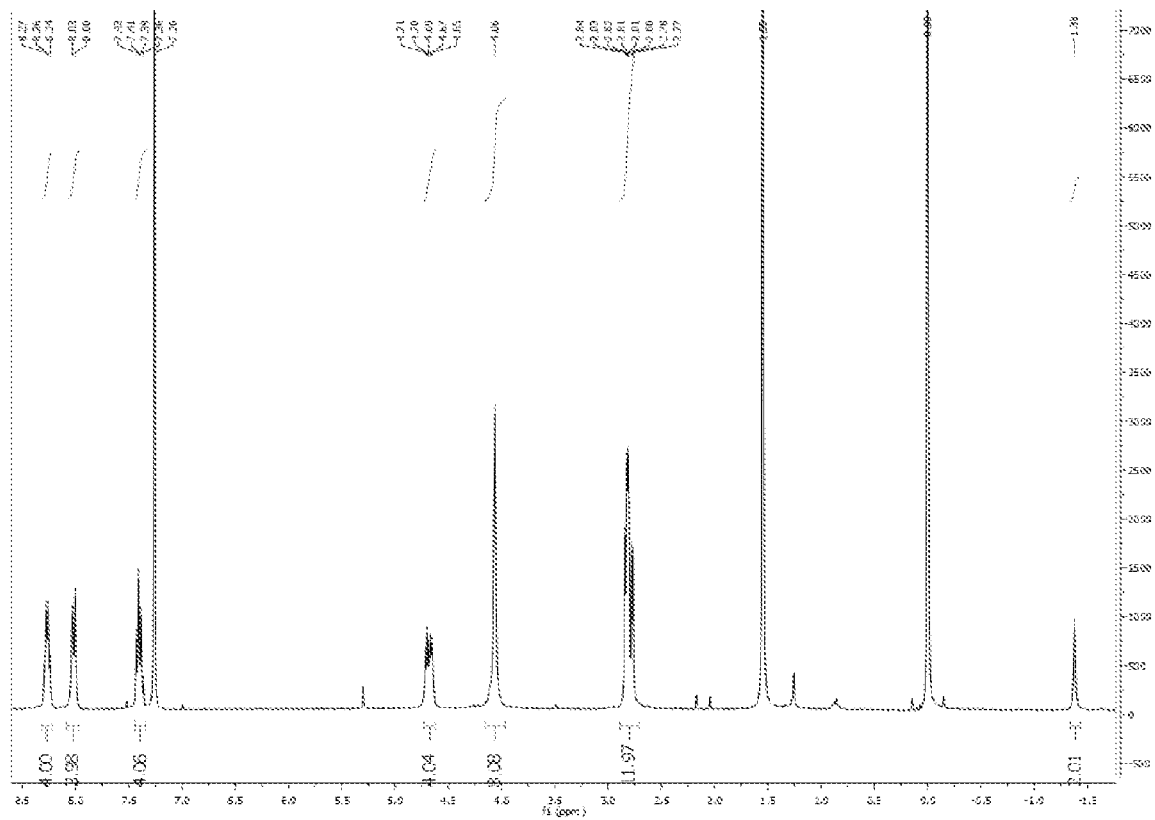
FIG. 8. $^1$H-NMR spectrum of LUZ11-B sample.

LUZ11-B (mostly α$_2$β$_2$):

NMR $^1$H (400 MHz, CDCl$_3$): δ, ppm: 8.27-8.24 (m, 4H, Ar—H); 8.03-8.00 (m, 4H, β-H); 7.43-7.36 (m, 4H, Ar—H); 4.71-4.65 (m, 4H, NH); 4.06 (s,8H, β-H); 2.84-2.77 (m, 12H, CH$_3$); -1.38 (s, 2H, NH). The NMR spectrum is shown in FIG. 8.

MS (ESI-FIA-TOF): m/z calcd for (C$_{48}$H$_{39}$F$_8$N$_8$O$_8$S$_4$) [M+H]$^+$: 1135.1640, found [M+H]$^+$: 1135.1586.

Elemental Analysis (C$_{48}$H$_{38}$F$_8$N$_8$O$_8$S$_4$): calcd. C 50.79, H 3.37, N 9.87, found C 50.98, H 3.67, N 9.47.

Figure 9:
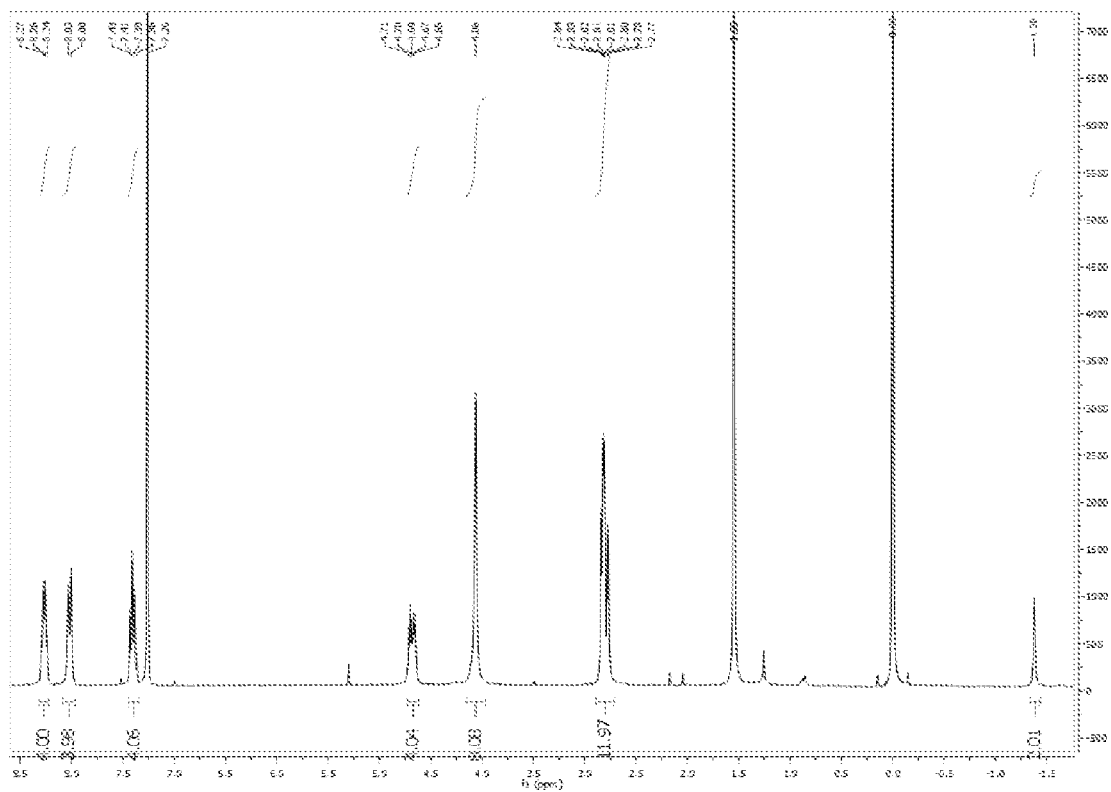
FIG. 9. $^1$H-NMR spectrum of LUZ11-C sample.

LUZ11-C (mostly α$_3$β):

NMR $^1$H (400 MHz, CDCl$_3$): δ, ppm: 8.27-8.24 (m, 4H, Ar—H); 8.03-8.00 (m, 4H, β-H); 7.43-7.36 (m, 4H, Ar—H); 4.71-4.65 (m, 4H, NH); 4.06 (s,8H, β-H); 2.84-2.77 (m, 12H, CH$_3$); -1.38 (s, 2H, NH). The NMR spectrum is shown in FIG. 9.

MS (ESI-FIA-TOF): m/z calcd for (C$_{48}$H$_{39}$F$_8$N$_8$O$_8$S$_4$) [M+H]$^+$: 1135.1640, found [M+H]$^+$: 1135.1657.

Elemental Analysis (C$_{48}$H$_{38}$F$_8$N$_8$O$_8$S$_4$.H$_2$O): calcd. C 50.79, H 3.37, N 9.87, found C 50.00, H 3.50, N 9.72.

Figure 10:
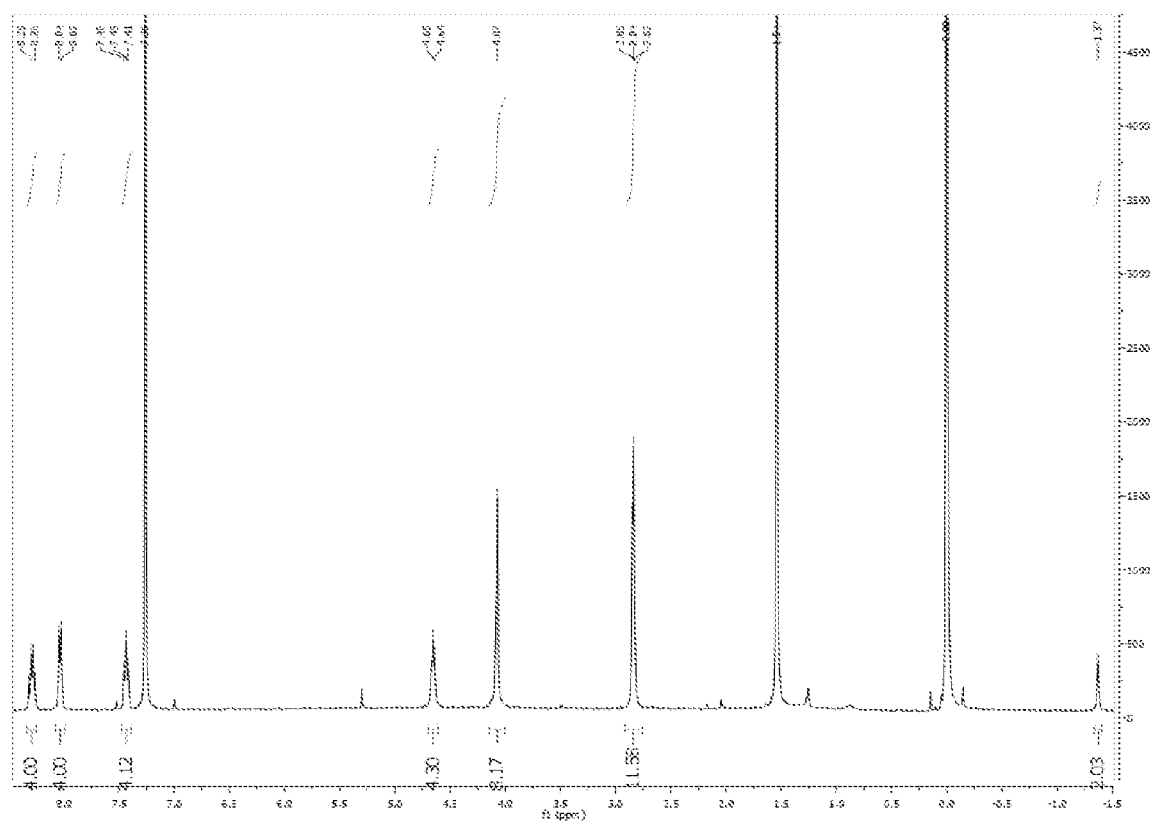
FIG. 10. $^1$H-NMR spectrum of LUZ11-D sample.

LUZ11-D (mostly α$_4$):

NMR $^1$H (400 MHz, CDCl$_3$): δ, ppm: 8.29-8.26 (m, 4H, Ar—H); 8.04-8.02 (m, 4H, β-H); 7.46-7.41 (m, 4H, Ar—H); 4.65-4.64 (m, 4H, NH); 4.07 (s,8H, β-H); 2.85-2.82 (m, 12H, CH$_3$); -1.37 (s, 2H, NH). The NMR spectrum is shown in FIG. 10.

MS (ESI-FIA-TOF): m/z calcd for (C$_{48}$H$_{39}$F$_8$N$_8$O$_8$S$_4$) [M+H]$^+$: 1135.1640, found [M+H]$^+$: 1135.1632.

Elemental Analysis (C$_{48}$H$_{38}$F$_8$N$_8$O$_8$S$_4$.H$_2$O): calcd. C 50.79, H 3.37, N 9.87, found C 50.38, H 3.66, N 9.13.

Figure 11:
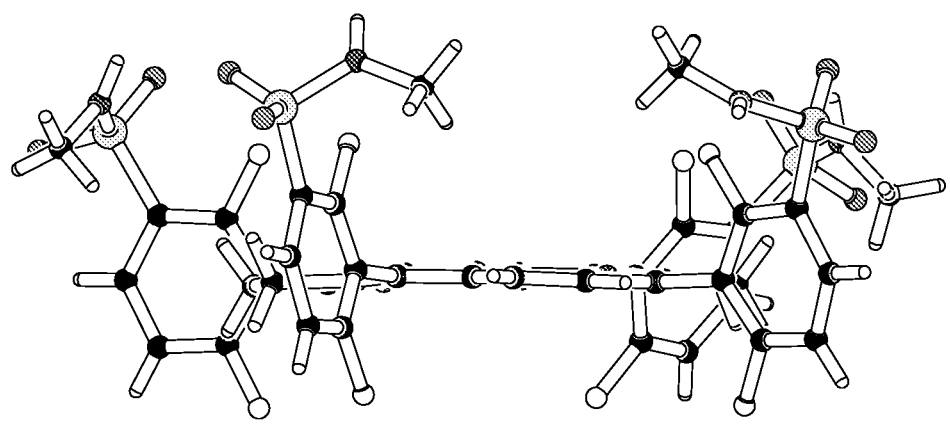
FIG. 11. X-ray structure of the $\alpha_4$ atropisomer of 5,10,15,20-tetrakis(2,6-difluoro-3-N-methylsulfamoylphenyl)bacteriochlorin, where the fluorine atoms are represented in yellow, the nitrogen atoms in blue, the sulfur atoms in green, the oxygen atoms in red and the carbon atoms in black.
Figure 12A:
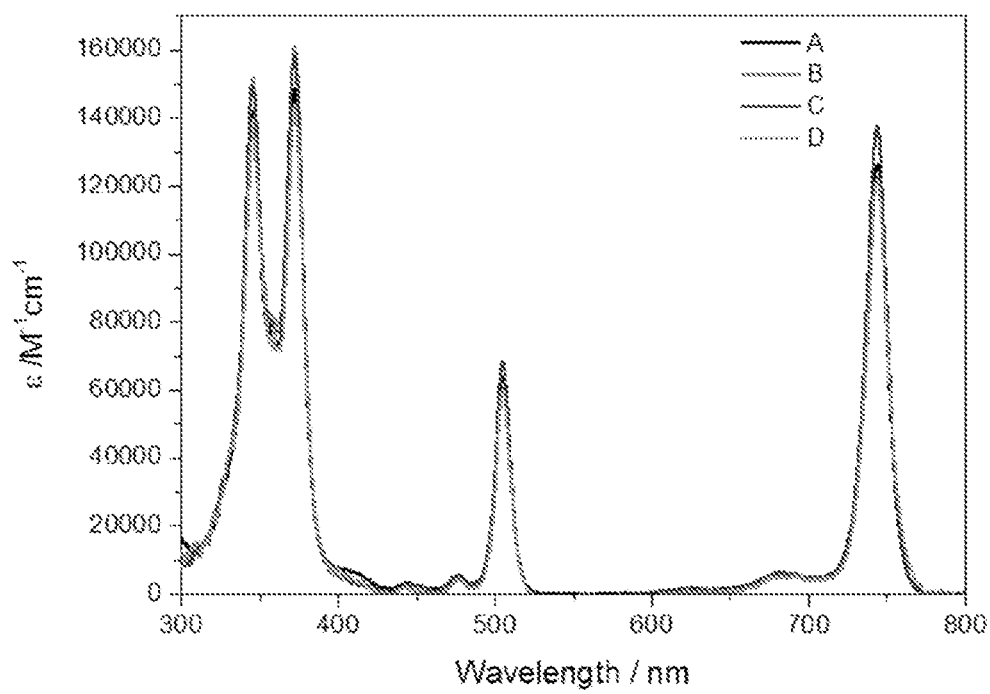
FIG. 12. A) Absorption spectra in ethanol of LUZ11-A, LUZ11-B, LUZ11-C and LUZ11-D samples. B) Beer-Lambert plots of the same samples used to calculate the molar absorption coefficients of the samples assuming that all the mass weighted is the mass of LUZ11.
Figure 12B:
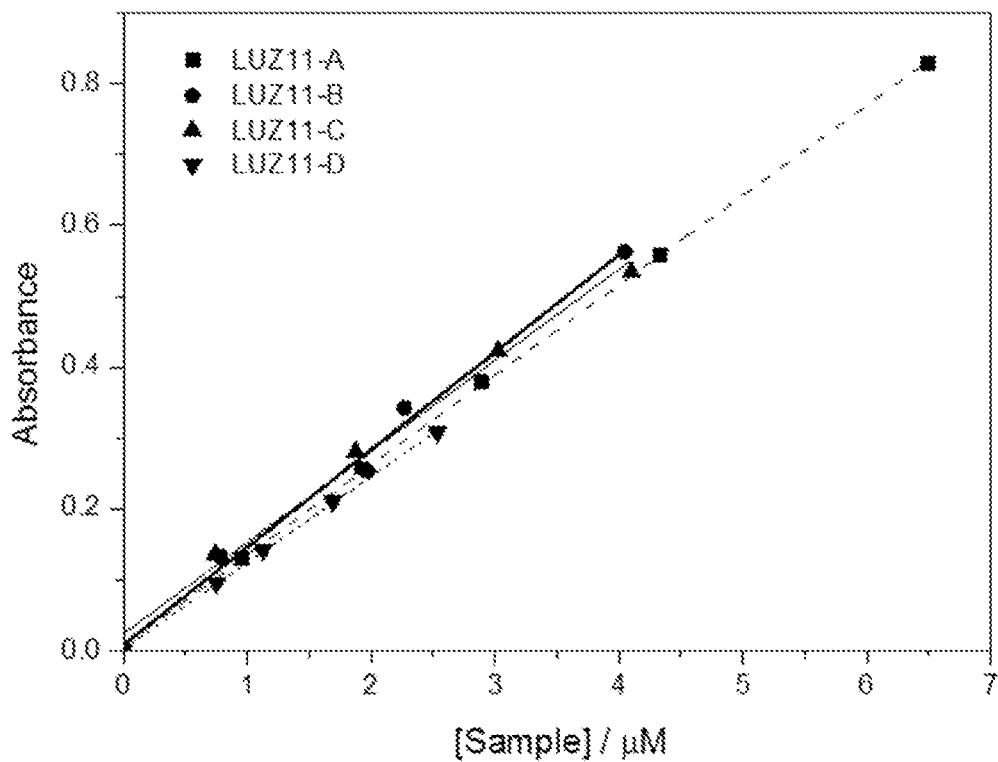

A crystal of the LUZ11-D atropisomer was obtained for X-ray structural determination in order to confirm the assignment. The X-ray structure obtained from the LUZ11-D is shown in FIG. 11 and confirms that this is the α$_4$ atropisomer. The photophysical properties of the samples LUZ11-A, LUZ11-B, LUZ11-C and LUZ11-D were determined using the instruments and methods described above. FIG. 12 presents the absorption spectra of the four samples. Table 1 collects the relevant data. FIG. 12 also presents the Beer-Lambert plots used to obtain the molar absorption coefficients of each sample, assuming that all the mass weighted to calculate the concentrations is the mass of LUZ11 atropisomers.

This example shows that the atropisomers α$_4$ and α$_3$β are sufficiently stable to be obtained with high purity using chemical separation processes at temperatures above 20° C. and in the presence of light and oxygen. The stability of these atropisomers was investigated heating the sample LUZ11-C in dimethylformamide at high temperatures and for various periods of time as illustrated in Table 3. The interconversion of the atropisomers occurs rapidly at high temperatures without appreciable decomposition of the fluorinated sulfonamide bacteriochlorin.

TABLE 3

Relative atropisomer contents after heating the LUZ11-C sample in dimethylformamide for the periods of time and temperatures indicated, and open to the atmosphere.

| | | Relative Atropisomer Proportion (%) | | | |
|---|---|---|---|---|---|
| Assay | Initial | Temperature Time 85° C. 12 h (% w/w) | Temperature Time 140° C. 5 min (% w/w) | Temperature Time 140° C. 10 min (% w/w) | Temperature Time 140° C. 20 min (% w/w) |
| Aβαβ | — | 5 | 14 | 9 | 12 |
| α$_2$β$_2$ | 1 | 14 | 19 | 20 | 23 |
| α$_3$β | 99 | 74 | 60 | 58 | 52 |
| α$_4$ | — | 7 | 5 | 11 | 11 |

Example 3

Enrichment of the Atropisomer Mixture using Selective Precipitation

This example shows that the mixture of atropisomers resulting from the synthesis of halogenated tetraphenylbacteriochlorins can be separated in fractions using simple and scalable methods and that one fraction is selectively enriched in atropisomers α$_3$β and α$_4$.

Figure 13:
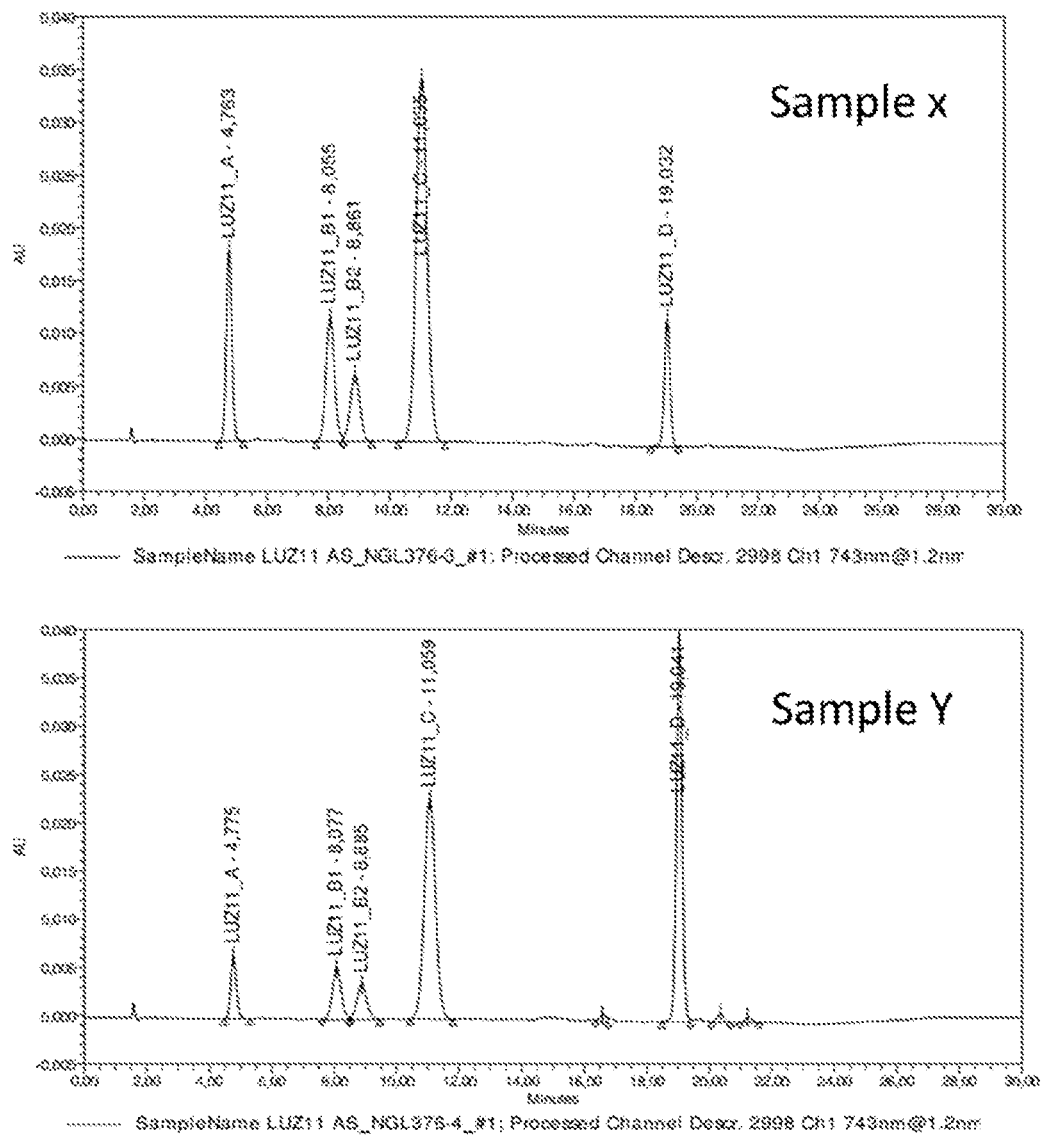
FIG. 13. HPLC chromatograms of fractions X and Y revealing the enrichment of fraction Y in the sum of atropisomers $\alpha_3\beta$ and $\alpha_4$.

Half a gram of LUZ11 is dissolved in 50 mL of dichloromethane in a round bottom flask. 50 mL of hexane are added and the flask is connected to a vacuum pump for 1 minute with gentle stirring. Some of the LUZ11 present in the solution precipitates in the flask. The sample is filtered giving the sample X. This solvent, containing dichloromethane and hexane, is evaporated until dryness giving the sample Y. Both samples were analyzed by HPLC in order to quantify the atropisomer relative amount in each sample. FIG. 13 presents the HPLC chromatograms with detection at 743 nm, described in the Methods section, revealing that the peaks of atropisomers αβαβ and α$_2$β$_2$ increase in sample X with respect to the original sample of LUZ11, and that the peak of the atropisomer α$_4$ increases in sample Y with respect to the original sample of LUZ11. Table 4 presents the relative amounts of the fours atropisomers present in the initial LUZ11 sample and in fractions X and Y. Atropisomer α$_2$β$_2$ has two peaks, identified as B1 and B2, because in bacteriochlorins the groups R' that are on the same side of the plane can be separated by a methine (=C—) group or by a methylene (—CH$_2$—) bridge. Whereas the original LUZ11 sample contains 65.9% of atropisomers α$_3$β+α$_4$, it is remarkable that sample Y contains 80.4% atropisomers α$_3$β+α$_4$.

Thus, sample Y is a composition where the atropisomers with most R' groups in the same side of the plane defined by the macrocycle constitute more than 70% of the total amount of atropisomers present in the composition.

TABLE 4

Relative atropisomer contents of LUZ11 sample and of samples X and Y.

| | Relative Atropisomer Proportion (%) | | |
|---|---|---|---|
| | LUZ11 | Sample X | Sample Y |
| Assay (% w/w) | 74.7% | 74.5% | 69.8% |
| Aβαβ | 13.2% | 14.0% | 6.1% |
| α$_2$β$_2$ | 20.9% | 23.0% | 13.5% |

TABLE 4-continued

Relative atropisomer contents of
LUZ11 sample and of samples X and Y.

| | Relative Atropisomer Proportion (%) | | |
|---|---|---|---|
| | LUZ11 | Sample X | Sample Y |
| $\alpha_3\beta$ | 53.0% | 53.4% | 42.0% |
| $\alpha_4$ | 12.9% | 9.6% | 38.4% |

The relative amount of atropisomers $\alpha_3\beta+\alpha_4$ in a sample can constitute any value up to 100% of the total amount of atropisomers present in the composition.

Example 4

Differential Stability of Atropisomers of Halogenated and Sulfonated Bacteriochlorins in the Presence of Infrared Light Absorbed This example demonstrates that atropisomers of halogenated and sulfonated bacteriochlorins have different photodecomposition quantum yields when irradiated with the same infrared light utilized in PDT, which may lead to differential PDT efficacies.

Figure 14:
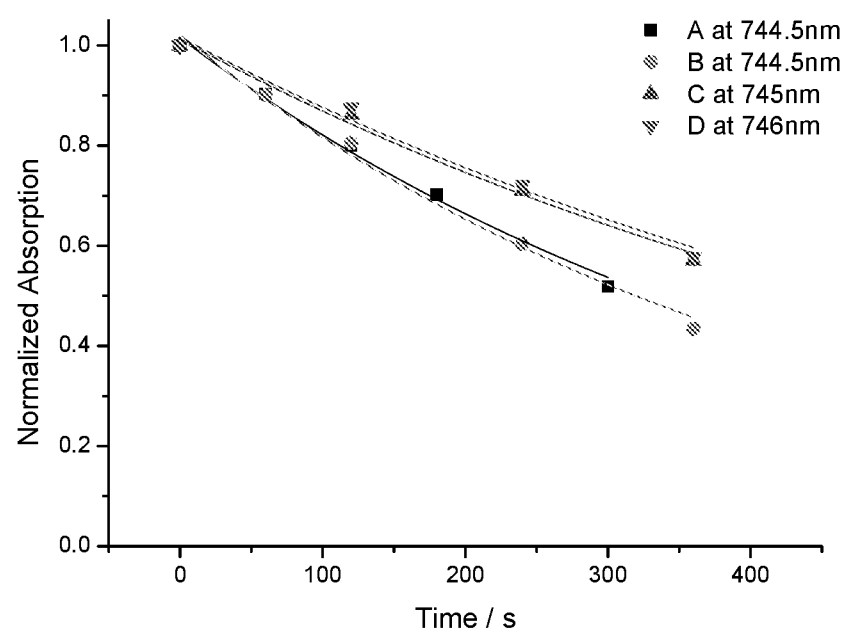
FIG. 14. Decay of the absorption at the peak of highest wavelength of samples of LUZ11-A (744.5 nm), LUZ11-B (744.5 nm), LUZ11-C (745 nm) and LUZ11-D (746 nm) in methanol:PBS (3:2), as a function of the duration of the irradiation.

LUZ11-A, LUZ11-B, LUZ11-C and LUZ11-D samples obtained in Example 2 above were independently dissolved in PBS:methanol (2:3) solutions, transferred to 1 cm quartz cells and their absorption spectra were registered. Each quartz cell was sequentially placed in the beam of the 749 nm Omicron diode laser, previously unfocused to have a beam diameter coincident with the window of the quartz cell. The laser power measured under these conditions was 640 mW. The irradiation was interrupted at regular time intervals and a new absorption spectrum was registered. The photobleaching follows the kinetics of a first-order reaction in the time window of the experiment. FIG. 14 shows the decay of the absorptions at the peak of highest wavelength of absorption of the samples as a function of the irradiation time. The half-lives of LUZ11-A, LUZ11-B, LUZ11-C and LUZ11-D samples under these conditions are 4.6, 4.8, 6.4 and 6.5 minutes respectively. The photodecomposition quantum yields were calculated as the initial rate of disappearance of the photosensitizer molecule divided by the initial rate of absorption of photons. The results of these calculations are presented in Table 1. The most stable atropisomer is $\alpha_4$, followed by $\alpha_3\beta$.

Example 5

In Vitro Phototoxicity of LUZ11 Atropisomers

This example shows that the samples LUZ11-A, LUZ11-B, LUZ11-C and LUZ11-D enriched in each of the isolated atropisomers and the original LUZ11 sample present differentiating PDT efficacies towards cancer cell lines.

The photosensitizing activity of the original LUZ11 sample and of the LUZ11-A, LUZ11-B, LUZ11-C and LUZ11-D samples obtained in Example 2 were measured with the materials and methods described before. HPLC chromatograms with detection at 380 nm indicate that the content of LUZ11 samples enriched in the separated atropisomer samples is higher than 80%. The small differences in purity do not bias the phototoxicity results.

Figure 15:
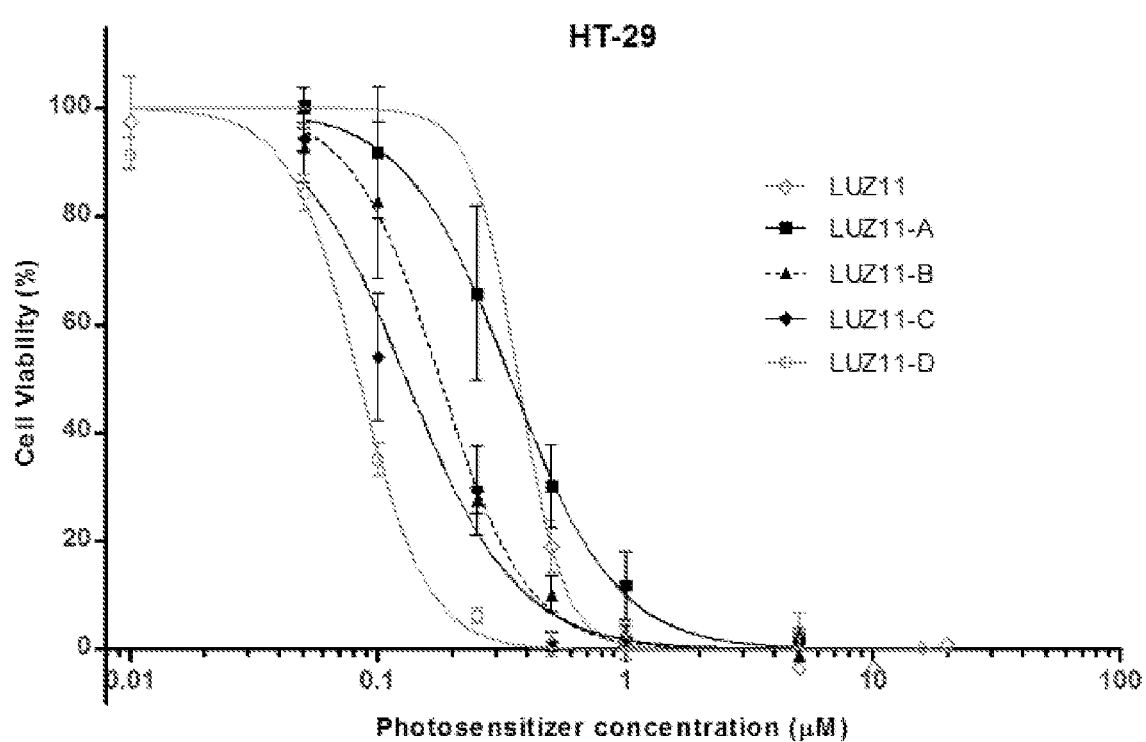
FIG. 15. Survival fractions of HT-29 cells for increasing photosensitizer doses of LUZ11, LUZ11-A, LUZ11-B, LUZ11-C and LUZ11-D samples and a constant light dose of 1 J/cm$^2$, used to obtain the IC50 and IC90 values presented in Table 5.
Figure 16:
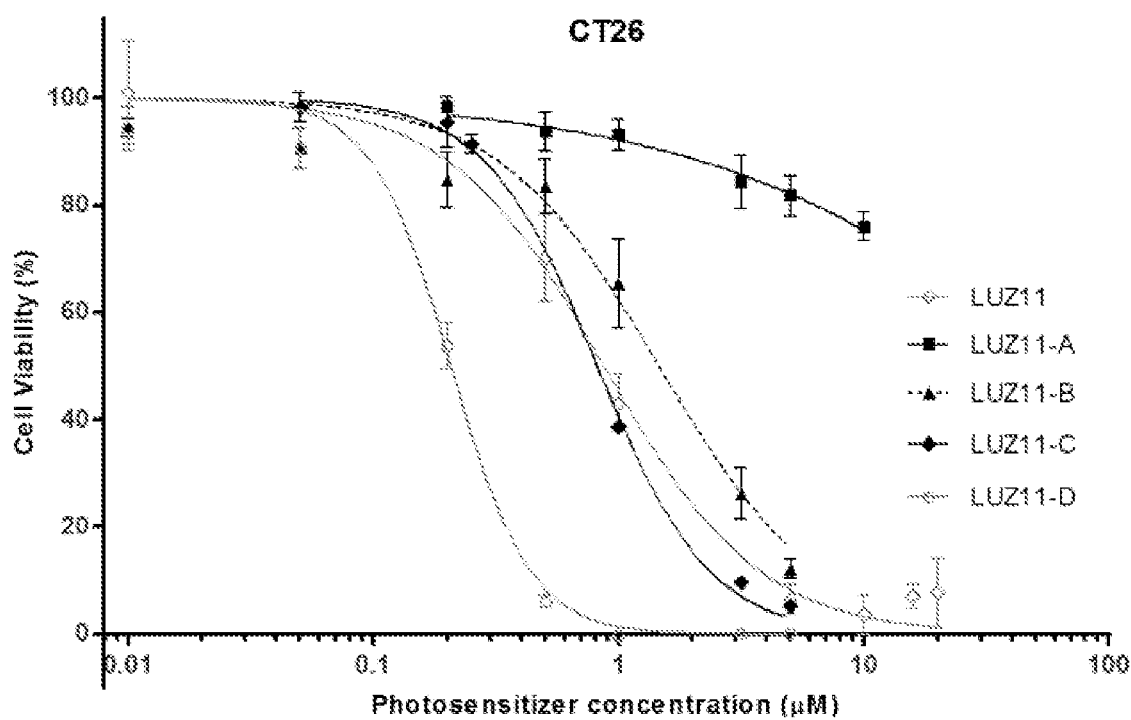
FIG. 16. Survival fractions of CT26 cells for increasing photosensitizer doses of LUZ11, LUZ11-A, LUZ11-B, LUZ11-C and LUZ11-D samples and a constant light dose of 1 J/cm$^2$, used to obtain the IC50 and IC90 values presented in Tables 1 and 5.

Survival fractions for light doses of 1 J/cm$^2$ and an incubation time of 24 hours, relative to control in the dark, are depicted in FIG. 15 (HT-29) and FIG. 16 (CT26). The concentrations that produced 50% or 90% of cell death for the light dose of 1 J/cm$^2$ are presented in Table 5 and were calculated by interpolation using non-linear regression analysis using GraphPad Prism 5 Software (log[inhibitor] versus normalized response—variable slope), except the values identified by an asterisk which were obtained by extrapolation.

TABLE 5

In vitro phototoxicity results for a light dose
of 1 J/cm$^2$ at 749 nm in terms of IC50 and IC90 for
each sample in the cell lines HT-29 and CT26.

| | HT-29 | | CT26 | |
|---|---|---|---|---|
| | IC50 (µM) | IC90 (µM) | IC50 (µM) | IC90 (µM) |
| LUZ11 | 0.367 | 0.588 | 0.871 | 4.307 |
| LUZ11-A | 0.343 | 1.006 | 67.35* | 2832* |
| LUZ11-B | 0.178 | 0.433 | 1.460 | 7.530* |
| LUZ11-C | 0.130 | 0.404 | 0.816 | 2.592 |
| LUZ11-D | 0.084 | 0.168 | 0.207 | 0.468 |

*Extrapolated from non-linear regression curve

The phototoxicities illustrated in FIGS. 15 and 16 and in Table 5 clearly demonstrate that LUZ11 atropisomers have differential in vitro PDT efficacy. The phototoxicity of the samples increases from A to D. The original LUZ11 sample, containing the statistical mixture of the atropisomers resulting from the synthesis, is less phototoxic in vitro than the samples enriched in atropisomers $\alpha_3\beta$ and $\alpha_4$. It is a major finding of this invention that the atropisomers with most of the meta substituents of the phenyl groups on the same side of the plane defined by the macrocycle are more phototoxic than the atropisomers with an equal number of such substituents on both sides of that plane. This finding could not have been anticipated by one of ordinary skill in the art.

Example 6

PDT of Mouse Colon Carcinoma in BALB/C Mice with LUZ11-A, LUZ11-B, LUZ11-C and LUZ11-D Atropisomers This example shows that each LUZ11 atropisomer presents a distinct long-term efficacy profile in the treatment of a mouse tumor model with PDT.

The tumor model was BALB/c mice with subcutaneous CT26 tumor. CT26 cells were cultured in DMEM medium supplemented with fetal bovine serum and antibiotics. The cells were grown at 37° C. in humidified atmosphere containing 5% CO$_2$. The CT26 cells (~350,000) were taken up in 0.1 ml PBS and implanted subcutaneously to the right thigh of the BALB/C mice. The tumors grew to reach 5 mm in diameter in about 8 to 10 days after the implantation. The treatment was initiated when the tumor attained 5 mm in diameter in each animal. The day the tumors reached the treatment size, the mice were injected with a dose of 0.7 mg/kg of the photosensitizer in a vehicle containing Cremophor EL (Macrogolglycerol Ricinoleate), ethanol and 0.9% NaCl saline solution in the proportions 0.1:0.5:99.4 for LUZ11 and LUZ11-A and 0.5:0.5:99.0 for LUZ11-B, LUZ11-C and LUZ11-D, and treated as described in the Methods section. The light fluence employed in the treatment was 41 J/cm$^2$ (i.e., 50 J on a 1.33 cm$^2$ surface). The doses of each compound were normalized taking into account the LUZ11 content of each sample. The control group (n=6) received only the vehicle, without photosensitizer, and was irradiated in the same conditions as the remaining test groups.

Figure 17:
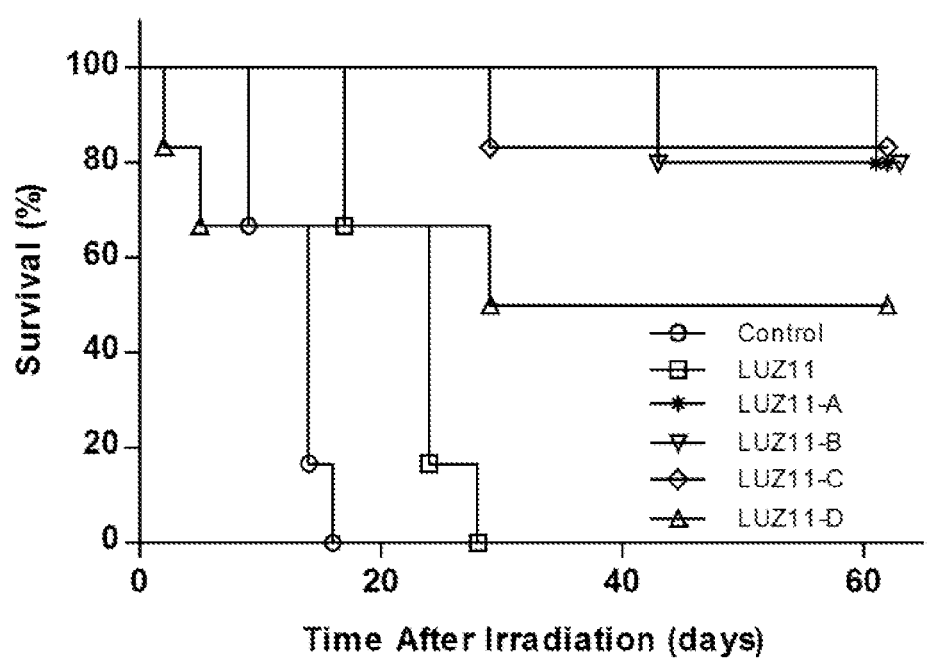
FIG. 17. Kaplan-Meier plot of CT26 tumor regrowth in BALB/C mice after PDT with 0.7 mg/kg of the photosensitizer indicated in the plot, and a light fluence of 41 J/cm$^2$. Mice that remained tumor-free 60 days after the treatment were considered cured.

The mice were checked daily, the tumors were measured using two orthogonal measurements L and W (perpendicular to L) and the volumes calculated using the formula V=L×W²/2 were recorded. When the longest diameter of any tumor reached 15 mm (humanitarian endpoint), the mouse bearing such tumor was sacrificed and the number of days elapsed since the treatment was recorded. FIG. 17 presents the Kaplan-Meier plot for the LUZ11, LUZ11-A, LUZ11-B, LUZ11-C and LUZ11-D samples of Example 2. The much higher phototoxicity of the atropisomer $\alpha_4$ is manifested by the PDT-induced death, in the LUZ11-D sample group, of 2 mice in the days subsequent to the treatment. Overdosing with the atropisomer $\alpha_4$ occurs at a drug-light dose combination without PDT-induced lethality for other atropisomer mixtures. This observation is consistent with the phototoxicity in vitro and shows that the atropisomer $\alpha_4$ has the highest PDT efficacy.

Example 7

PDT of Mouse Colon Carcinoma in BALB/C Mice with Enriched Atropisomer Compositions This example shows that a pharmaceutical composition enriched in the more photoactive atropisomers is preferred for PDT because it presents the best long-term efficacy profile in the treatment of a mouse tumor model with PDT.

Figure 18:
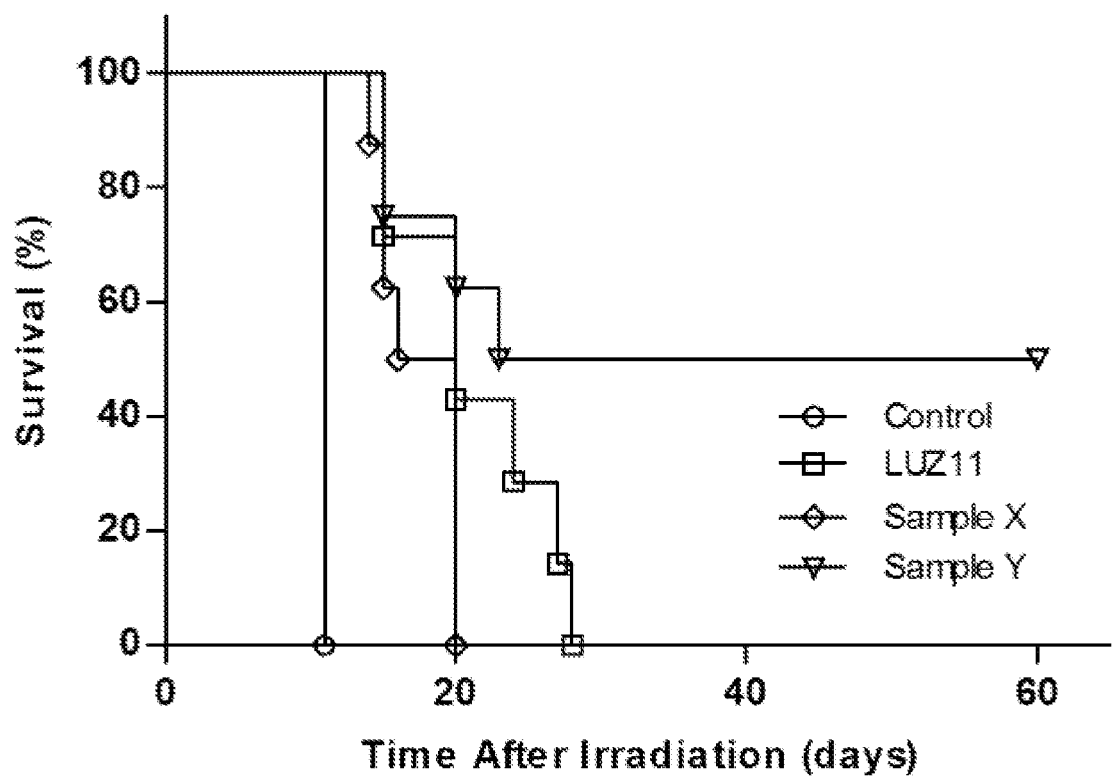
FIG. 18. Kaplan-Meier plot of CT26 tumor regrowth in BALB/C mice after PDT with 0.7 mg/kg of the atropisomer compositions indicated in the plot, and a light fluence of 41 J/cm$^2$. Mice that remained tumor-free 60 days after the treatment were considered cured. Sample X and Sample Y are from Example 3.

The mouse and tumor model is the same as in Example 6. PDT was also performed with the same protocol: intravenous injection of a nominal photosensitizer dose of 0.7 mg/kg followed 15 minutes later with the irradiation of a 1.33 cm² circle with 55 J. This nominal concentration, by weight of the sample, corresponds to a concentration of 0.52 mg/kg of the actual amount of bacteriochlorin stereoisomers present in the samples LUZ11, LUZ11-X, relative to sample X, and LUZ11-Y, relative to sample Y. The vehicle employed for the intravenous administration was the same as in Example 6 but the samples X and Y of Example 3 were employed, in parallel with the LUZ11 sample characterized in Table 4. FIG. 18 presents the Kaplan-Meier plot for the LUZ11 sample, and samples X and Y.

FIG. 18 shows that with the original fraction of LUZ11 is not possible to obtain long-term cures with this treatment protocol. The absence of long-term cures was also observed in the group treated with sample X. Furthermore, the median survival time in the treatment with sample X was 2 days shorter (18 vs. 20 days) than the medium survival time with the LUZ11 sample. On the other hand, the group treated with sample Y had a longer median survival time and attained a cure rate of 50%.

The remarkable ability of pharmaceutical compositions with atropisomer mixtures enriched in atropisomers $\alpha_3\beta$ and $\alpha_4$ to improve cure rates in PDT is unexpected and are disclosed for the first time in this invention.

Example 8

Isolation of LUZ11-C ($\alpha 3\beta$) Atropisomer by Reverse Phase Classical Column Chromatography and Semi-Preparative HPLC The purification of LUZ11-C was performed in two steps: i) sample enrichment on $\alpha_3\beta$ from the mixture of the four atropisomers ($\alpha\beta\alpha\beta$, $\alpha_2\beta_2$, $\alpha_3\beta$, $\alpha_4$ and synthesis impurities) by using reverse phase silica gel (C-18) gravity chromatography, as stationary phase, with a mixture of MeOH/CN₃CN/H₂O (40:40:20, v/v) as mobile phase; ii) purification of the previously obtained $\alpha_3\beta$ enriched mixture by semi-preparative HPLC.

i) LUZ11—C ($\alpha_3\beta$) Enrichment by Reverse Phase Chromatography

LUZ11 (1 g; assay 75%) was dissolved in acetonitrile (10 mL) and methanol (10 mL), and the mixture was sonicated for 5 min. After total solubilization, 5 mL of water was slowly added. A glass column chromatography (d=3.5 cm*h=65 cm) was prepared using a slurry of eluent (MeOH/CN₃CN/H₂O (40:40:20, v/v)) and the C-18 reverse-phase silica (~150 g). The prepared sample of LUZ11 was carefully transferred to the column. The mobile phase mixture was slowly eluted through the column and the fractions containing the $\alpha_3\beta$ atropisomer were collected. During the whole chromatographic procedure, the glass column chromatography was protected from light as well as the collected fractions. The organic solvent was removed in the rotary evaporator (T<35° C.). The mixture was transferred to an extraction funnel and LUZ11-C was recovered by solvent-solvent extraction using dichloromethane. The organic phase was dried and solvent was removed by rotary evaporation (T<35° C.). The flask with product was connected to a vacuum pump for at least 72 h at 18-23° C. protected from light. About 300 mg of LUZ11-C was obtained.

ii) LUZ11—C ($\alpha_3\beta$) Isolation by Semi-Preparative HPLC

A sample (300 mg) of LUZ11-C ($\alpha_3\beta$) enriched fraction, previously prepared by C-18 reverse phase silica gel, was dissolved in 12 mL of DMF and 2.5 mL of water and sonicated for 5 minutes or until complete solubilization. The HPLC conditions for LUZ11-C isolation are described below:

Column: Inertsil-Phenyl (250*10 mm; 5 μm)
Flow: 3 mL/min
Detection: Vis 743 nm
Oven: 23° C.
Injection volume: 100 μL
Run time: 70 min
Mobile phase: Mobile Phase A: Acetonitrile Gradient Grade
Mobile Phase B: Water

TABLE 6

| Gradient Program: | | |
| --- | --- | --- |
| Time (min) | Mobile Phase A | Mobile Phase B |
| 0 | 57 | 43 |
| 50 | 57 | 43 |
| 54 | 95 | 5 |
| 65 | 95 | 5 |
| 68 | 57 | 43 |
| 70 | 57 | 43 |

The mixture was transferred to an extraction funnel and LUZ11-C was recovered by solvent-solvent extraction using dichloromethane. The organic phase was dried and the solvent was removed by rotary evaporation (T<35° C.). The flask with product was connected to a vacuum pump for at least 72 h at 18-23° C. protected from light. Using this method LUZ11-C was obtained with assay between 94% and 96%. The impurity profile of this LUZ11-C ($\alpha_3\beta$) enriched fraction showed that $\alpha\beta\alpha\beta$, $\alpha_2\beta_2$, and $\alpha_4$ atropisomers were present in less than 2%.

DOCUMENTS CITED

1. M. M. Pereira, L. G. Arnaut, S. J. Formosinho, C. J. P. Monteiro, PCT/EP/012212, Ed. (University of Coimbra, Portugal, 2005), chap. PCT/EP/012212.
2. L. G. Arnaut, M. M. Pereira, S. J. Formosinho, S. Simões, G. Stochel, K. Urbanska, PCT/PT2009/000057, Ed. (University of Coimbra, Portugal, 2009), chap. PCT/PT2009/000057.
3. J. M. Dabrowski, M. Krzykawska, L. G. Arnaut, M. M. Pereira, C. J. P. Monteiro, S. Simoes, K. Urbanska, G. Stochel, Tissue uptake and photodynamic therapy of mice bearing melanoma with a non-toxic, effective chlorin. Chem Med Chem 6, 1715-1726 (2011).
4. L. G. Arnaut, M. M. Pereira, J. M. Dabrowski, E. F. F. Silva, F. A. Schaberle, A. R. Abreu, L. B. Rocha, M. M. Barsan, K. Urbanska, G. Stochel, C. M. A. Brett, Photodynamic Therapy Efficacy Enhanced by Dynamics: The Role of Charge Transfer and Photostability in the Selection of Photosensitizers. Chem. Eur. J. 20, 5346-5357 (2014).
5. L. G. Arnaut, Design of Porphyrin-Based Photosensitizers. Adv. Inorg. Chem. 63, 187-233 (2011).
6. S. R. LaPlante, P. J. Edwards, L. D. Fader, A. Jakalian, O. Hucke, Revealing atropisomer axial chirality in drug discovery. Chem Med Chem 6, 505-513 (2011).
7. A. S. M. Ressurreição, M. Pineiro, L. G. Arnaut, A. M. d. A. R. Gonsalves, Atropisomers of 5,10,15,20-tetrakis(2,6-dichloro-3-sulfamoyl-phenyl)porphyrins J. Porphyrins Phthalocyanines 11, 50-57 (2007).
8. A. C. Tomé, A. M. S. Silva, I. Alkorta, J. Elguero, Atropisomerism and corformational aspectes of meso-tetraarylporphyrins and related compounds. J. Phorphyrins Phthalocyanines 15, 1-28 (2011).
9. C. J. P. Monteiro, M. M. Pereira, N. Gonçalves, C. G. Carvalho, A. R. Abreu, L. G. Arnaut, A. M. S. Silva, Separation and atropisomer isolation of ortho-halogenated tetraarylporphyrins by HPLC. Full characterization using 1D and 2D NMR. J. Porphyrins Phthalocyanines 16, 316-323 (2012).
10. W. J. Hagan, D. C. Barber, D. G. Whitten, M. Kelly, F. Albrecht, S. L. Gibson, R. Hilf, Picket-fence porphyrins as potential phototherapeutic agents. Cancer Res. 48, 1148-1152 (1988).
11. C. J. P. Monteiro, J. Pina, M. M. Pereira, L. G. Arnaut, On the singlet states of porphyrins, chlorins and bacteriochlorins and their ability to harvest red/infrared light. Photochem. Photobiol. Sci. 11, 1233-1238 (2012).
12. E. F. F. Silva, C. Serpa, J. M. Dabrowski, C. J. P. Monteiro, L. G. Arnaut, S. J. Formosinho, G. Stochel, K. Urbanska, S. Simoes, M. M. Pereira, Mechanisms of singlet oxygen and superoxide ion generation by porphyrins and bacteriochlorins. Chem. Eur. J. 16, 9273-9286 (2010).
13. J. M. Dabrowski, M. M. Pereira, L. G. Arnaut, C. J. P. Monteiro, A. F. Peixoto, A. Karocki, K. Urbanska, G. Stochel, Synthesis, photophysical studies and anticancer activity of a new halogenated water-soluble porphyrin. Photochem. Photobiol. 83, 897-903 (2007).
14. R. Schmidt, C. Tanielian, R. Dunsbach, C. Wolff, Phenalenone, a universal reference compounds for the determination of quantum yields of singlet oxygen. J. Photochem. Photobiol. A: Chem. 79, 11-17 (1994).
15. Sternberg E D, Dolphin D. Porphyrin-based photosensitizers for use in photodynamic therapy. Tetrahedron 1998; 54:4151-202.
16. Silva E F F, Serpa C, Dabrowski J M, Monteiro C J P, Arnaut L G, Formosinho S J, et al. Mechanisms of singlet oxygen and superoxide ion generation by porphyrins and bacteriochlorins. Chem Eur J. 2010; 16:9273-86.

The invention claimed is:
1. A pharmaceutical composition comprising atropisomers of the formulae:

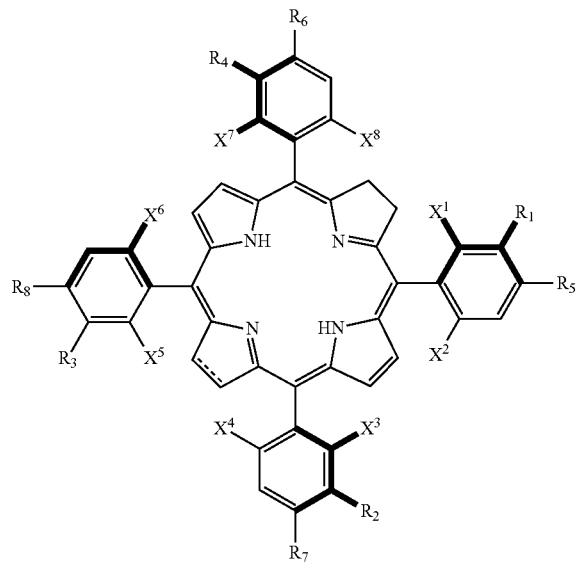

Formula (I-C)

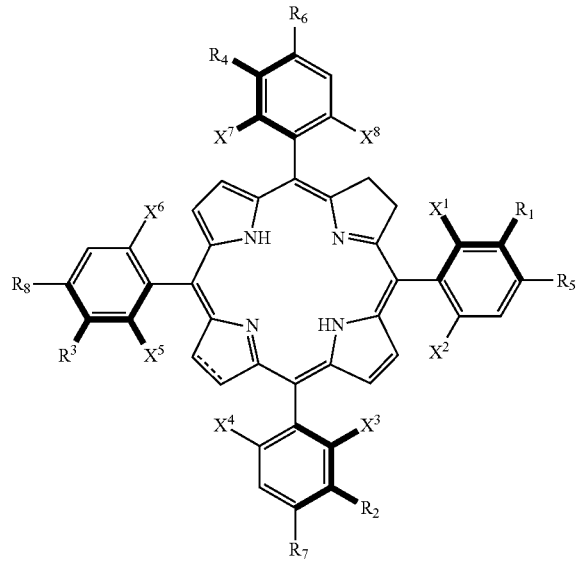

Formula (I-D)

===== represents a carbon-carbon single bond or a carbon-carbon double bond;
the bold lines indicate that the bolded atoms, and the groups attached thereto, are sterically restricted so as to exist above the plane defined by the macrocycle ring;
$X^2$, $X^4$, $X^6$ and $X^8$ are each F;
$X^1$, $X^3$, $X^5$ and $X^7$ are each F;

$R_1$, $R_2$, $R_3$ and $R_4$ are independently $SO_2R''$, wherein $R''$ is —NHR, wherein R is an alkyl of 1 to 12 carbon atoms;

$R_5$, $R_6$, $R_7$ and $R_8$ are independently H;

or pharmaceutically acceptable salts thereof;

wherein the relative amount of said atropisomers or their pharmaceutically acceptable salts is at least 80% of the total of atropisomers in the referred pharmaceutical composition.

2. The pharmaceutical composition according to claim 1, wherein the relative amount of the atropisomer of the formulae:

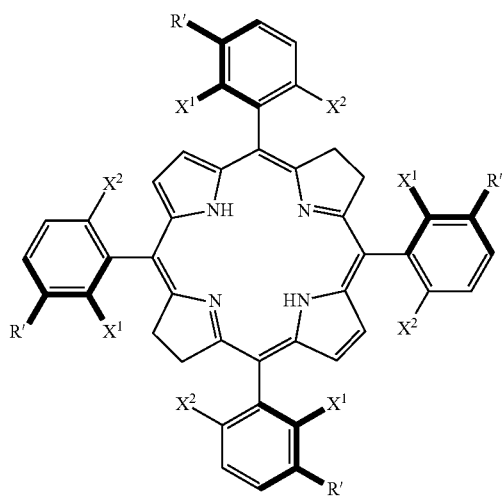

Formula (III-D)

wherein:

the bold lines indicate that the bolded atoms, and the groups attached thereto, are sterically restricted so as to exist above the plane defined by the macrocycle ring;

$X^2$ is F;

$X^1$ is F; and

R' is —$SO_2R''$, wherein R'' is —NHR wherein R is an alkyl of 1 to 12 carbon atoms;

or its pharmaceutically acceptable salts thereof;

is more than 20% of the total of atropisomers in the referred pharmaceutical composition.

3. The pharmaceutical composition according to claim 1, wherein the relative amounts of the atropisomer of the formulae:

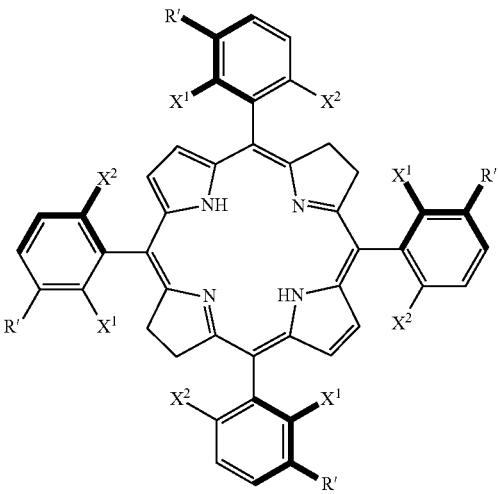

Formula (III-C)

wherein:

the bold lines indicate that the bolded atoms, and the groups attached thereto, are sterically restricted so as to exist above the plane defined by the macrocycle ring;

$X^2$ is F;

$X^1$ is F; and

R' is —$SO_2R''$, wherein R'' is, —NHR wherein R is an alkyl of 1 to 12 carbon atoms;

or its pharmaceutically acceptable salts thereof;

is more than 60% of the total of atropisomers in the referred pharmaceutical composition.

4. The pharmaceutical composition according to claim 1, wherein the pharmaceutical composition further comprises a pharmaceutical carrier.

5. A kit comprising a pharmaceutical composition described in claim 1 and instructions for photodynamic therapy/administration of the composition to a subject.

6. The pharmaceutical composition according to claim 3, wherein the relative amounts of the atropisomer of the Formula III-C is more than 70% of the total atropisomers in the referred pharmaceutical composition.

7. The pharmaceutical composition according to claim 3, wherein the relative amounts of the atropisomer of the Formula III-C is more than 80% of the total atropisomers in the referred pharmaceutical composition.

8. The pharmaceutical composition according to claim 3, wherein the relative amounts of the atropisomer of the Formula III-C is more than 90% or 95% of the total atropisomers in the referred pharmaceutical composition.

* * * * *